United States Patent
Hinton et al.

(10) Patent No.: US 10,864,033 B2
(45) Date of Patent: **\*Dec. 15, 2020**

(54) SECURE CRYOSURGICAL TREATMENT SYSTEM

(71) Applicant: Pacira CryoTech, Inc., Parsippany, NJ (US)

(72) Inventors: Corydon A. Hinton, Oakland, CA (US); Kyler Mikhail Connelly, Castro Valley, CA (US); Bijy Zachariah, Fremont, CA (US); Jesse Rosen, Albany, CA (US)

(73) Assignee: Pacira CryoTech, Inc., Parsippany, NJ (US)

( * ) Notice: Subject to any disclaimer, the term of this patent is extended or adjusted under 35 U.S.C. 154(b) by 105 days.

This patent is subject to a terminal disclaimer.

(21) Appl. No.: 16/168,551

(22) Filed: Oct. 23, 2018

(65) Prior Publication Data

US 2019/0125423 A1 May 2, 2019

Related U.S. Application Data

(63) Continuation of application No. 14/534,120, filed on Nov. 5, 2014, now Pat. No. 10,130,409.

(Continued)

(51) Int. Cl.
*A61B 18/02* (2006.01)
*A61B 18/00* (2006.01)
(Continued)

(52) U.S. Cl.
CPC .............. *A61B 18/02* (2013.01); *A61B 34/25* (2016.02); *A61B 90/90* (2016.02);
(Continued)

(58) Field of Classification Search
CPC .......... A61B 18/02; A61B 2017/00199; A61B 2017/0023; A61B 2017/00482;
(Continued)

(56) References Cited

U.S. PATENT DOCUMENTS 2,319,542 A 5/1943 Hall
2,672,032 A 3/1964 Towse
(Continued)

FOREIGN PATENT DOCUMENTS

CA 2643474 9/2007
EP 0043447 1/1982
(Continued)

OTHER PUBLICATIONS

Advanced Cosmetic Intervention, Inc. webpage, retrieved from the internet at http://www.acisurgery.com, 2007, 1 page.
(Continued)

*Primary Examiner* — George Manuel
(74) *Attorney, Agent, or Firm* — Kilpatrick Townsend & Stockton LLP

(57) ABSTRACT

A method for cryogenically treating tissue. A connection is detected between a probe having a disposable secure processor (DSP) to a handpiece having a master control unit (MCU) and a handpiece secure processor (HSP), the probe having at least one cryogenic treatment applicator. The probe is fluidly coupled to a closed coolant supply system within the handpiece via the connection. An authentication process is initiated between the DSP and the HSP using the MCU. As a result of the authentication process, one of at least two predetermined results is determined, the at least two predetermined results being that the probe is authorized and non-authorized.

32 Claims, 14 Drawing Sheets

Related U.S. Application Data

(60) Provisional application No. 61/900,345, filed on Nov. 5, 2013.

(51) Int. Cl.
    *A61B 17/00*      (2006.01)
    *A61B 34/00*      (2016.01)
    *A61B 90/90*      (2016.01)
    *A61B 90/00*      (2016.01)

(52) U.S. Cl.
    CPC .......... *A61B 2017/0023* (2013.01); *A61B 2017/00199* (2013.01); *A61B 2017/00482* (2013.01); *A61B 2018/00041* (2013.01); *A61B 2018/00714* (2013.01); *A61B 2018/00744* (2013.01); *A61B 2018/00791* (2013.01); *A61B 2018/00922* (2013.01); *A61B 2018/00988* (2013.01); *A61B 2018/0262* (2013.01); *A61B 2018/0268* (2013.01); *A61B 2018/0293* (2013.01); *A61B 2090/0803* (2016.02); *A61B 2090/0814* (2016.02)

(58) Field of Classification Search
    CPC ........ A61B 2018/00041; A61B 2018/00714; A61B 2018/00744; A61B 2018/00791; A61B 2018/00922; A61B 2018/00988; A61B 2018/0262; A61B 2018/0268; A61B 2018/0293; A61B 2090/0803; A61B 2090/0814; A61B 34/25; A61B 90/90
    See application file for complete search history.

(56) References Cited

U.S. PATENT DOCUMENTS

| | | |
|---|---|---|
| 3,266,492 A | 8/1966 | Steinberg |
| 3,289,424 A | 12/1966 | Shepherd |
| 3,343,544 A | 9/1967 | Dunn et al. |
| 3,351,063 A | 11/1967 | Malaker et al. |
| 3,439,680 A | 4/1969 | Thomas, Jr. |
| 3,483,869 A | 12/1969 | Hayhurst |
| 3,507,283 A | 4/1970 | Thomas, Jr. |
| 3,532,094 A | 10/1970 | Stahl |
| 3,664,344 A | 5/1972 | Bryne |
| 3,702,114 A | 11/1972 | Zacarian |
| 3,795,245 A | 3/1974 | Allen, Jr. et al. |
| 3,814,095 A | 6/1974 | Lubens |
| 3,830,239 A | 8/1974 | Stumpf et al. |
| 3,886,945 A | 6/1975 | Stumpf et al. |
| 3,889,681 A | 6/1975 | Waller et al. |
| 3,951,152 A | 4/1976 | Crandell et al. |
| 3,993,075 A | 11/1976 | Lisenbee et al. |
| 4,140,109 A | 2/1979 | Savic et al. |
| 4,207,897 A | 6/1980 | Lloyd et al. |
| 4,236,518 A | 12/1980 | Floyd |
| 4,306,568 A | 12/1981 | Torre |
| 4,376,376 A | 3/1983 | Gregory |
| 4,404,862 A | 9/1983 | Harris, Sr. |
| 4,524,771 A | 6/1985 | McGregor et al. |
| 4,758,217 A | 7/1988 | Gueret |
| 4,802,475 A | 2/1989 | Weshahy |
| 4,946,460 A | 8/1990 | Merry et al. |
| 5,059,197 A | 10/1991 | Urie et al. |
| 5,200,170 A | 4/1993 | McDow |
| 5,294,325 A | 3/1994 | Liu |
| 5,334,181 A | 8/1994 | Rubinsky et al. |
| 5,520,681 A | 5/1996 | Fuller et al. |
| 5,571,147 A | 11/1996 | Sluijter et al. |
| 5,647,868 A | 7/1997 | Chinn |
| 5,747,777 A | 5/1998 | Matsuoka |
| 5,755,753 A | 5/1998 | Knowlton |
| 5,814,040 A | 9/1998 | Nelson et al. |
| 5,860,970 A | 1/1999 | Goddard et al. |
| 5,879,378 A | 3/1999 | Usui |
| 5,899,897 A | 5/1999 | Rabin et al. |
| 5,916,212 A | 6/1999 | Baust et al. |
| 5,976,505 A | 11/1999 | Henderson |
| 6,003,539 A | 12/1999 | Yoshihara |
| 6,032,675 A | 3/2000 | Rubinsky |
| 6,039,730 A | 3/2000 | Rabin et al. |
| 6,041,787 A | 3/2000 | Rubinsky |
| 6,139,545 A | 10/2000 | Utley et al. |
| 6,141,985 A | 11/2000 | Cluzeau et al. |
| 6,142,991 A | 11/2000 | Schatzberger |
| 6,182,666 B1 | 2/2001 | Dobak, III |
| 6,196,839 B1 | 3/2001 | Ross |
| 6,238,386 B1 | 5/2001 | Mueller et al. |
| 6,277,099 B1 | 8/2001 | Strowe et al. |
| 6,277,116 B1 | 8/2001 | Utely et al. |
| 6,363,730 B1 | 4/2002 | Thomas et al. |
| 6,371,943 B1 | 4/2002 | Racz et al. |
| 6,432,102 B2 | 8/2002 | Joye et al. |
| 6,494,844 B1 | 12/2002 | Van Bladel et al. |
| 6,503,246 B1 | 1/2003 | Har-Shai et al. |
| 6,506,796 B1 | 1/2003 | Fesus et al. |
| 6,546,935 B2 | 4/2003 | Hooven |
| 6,551,309 B1 | 4/2003 | Lepivert |
| 6,562,030 B1 | 5/2003 | Abboud et al. |
| 6,629,951 B2 | 10/2003 | Laufer et al. |
| 6,648,880 B2 | 11/2003 | Chauvet et al. |
| 6,669,688 B2 | 12/2003 | Svaasand et al. |
| 6,672,095 B1 | 1/2004 | Luo |
| 6,682,501 B1 | 1/2004 | Nelson et al. |
| 6,706,037 B2 | 3/2004 | Zvuloni et al. |
| 6,723,092 B2 | 4/2004 | Brown et al. |
| 6,749,624 B2 | 6/2004 | Knowlton |
| 6,761,715 B2 | 7/2004 | Carroll |
| 6,764,493 B1 | 7/2004 | Weber et al. |
| 6,786,901 B2 | 9/2004 | Joye et al. |
| 6,786,902 B1 | 9/2004 | Rabin et al. |
| 6,789,545 B2 | 9/2004 | Littrup et al. |
| 6,840,935 B2 | 1/2005 | Lee |
| 6,858,025 B2 | 2/2005 | Maurice |
| 6,902,554 B2 | 6/2005 | Huttner |
| 6,905,492 B2 | 6/2005 | Zvuloni et al. |
| 6,960,208 B2 | 11/2005 | Bourne et al. |
| 7,001,400 B1 | 2/2006 | Modesitt et al. |
| 7,081,111 B2 | 7/2006 | Svaasand et al. |
| 7,081,112 B2 | 7/2006 | Joye et al. |
| 7,083,612 B2 | 8/2006 | Littrup et al. |
| 7,195,616 B2 | 3/2007 | Diller et al. |
| 7,204,833 B1 | 4/2007 | Osorio et al. |
| 7,217,939 B2 | 5/2007 | Johansson et al. |
| 7,250,046 B1 | 7/2007 | Fallat |
| 7,311,672 B2 | 12/2007 | Van Bladel et al. |
| 7,367,341 B2 | 5/2008 | Anderson et al. |
| 7,402,140 B2 | 7/2008 | Spero et al. |
| 7,422,586 B2 | 9/2008 | Morris et al. |
| 7,578,819 B2 | 8/2009 | Bleich et al. |
| 7,641,679 B2 | 1/2010 | Joye et al. |
| 7,713,266 B2 | 5/2010 | Elkins et al. |
| 7,850,683 B2 | 12/2010 | Elkins et al. |
| 7,862,558 B2 | 1/2011 | Elkins et al. |
| 7,998,137 B2 | 8/2011 | Elkins et al. |
| 8,298,216 B2 | 10/2012 | Burger et al. |
| 8,409,185 B2 | 4/2013 | Burger et al. |
| 8,715,275 B2 | 5/2014 | Burger et al. |
| 2002/0010460 A1 | 1/2002 | Joye et al. |
| 2002/0013602 A1 | 1/2002 | Huttner |
| 2002/0045434 A1 | 4/2002 | Masoian et al. |
| 2002/0049436 A1 | 4/2002 | Zvuloni et al. |
| 2002/0068929 A1 | 6/2002 | Zvuloni |
| 2002/0120260 A1 | 8/2002 | Morris et al. |
| 2002/0120261 A1 | 8/2002 | Morris et al. |
| 2002/0120263 A1 | 8/2002 | Brown et al. |
| 2002/0128638 A1 | 9/2002 | Chauvet et al. |
| 2002/0156469 A1 | 10/2002 | Yon et al. |
| 2002/0183731 A1 | 12/2002 | Holland et al. |
| 2002/0193778 A1 | 12/2002 | Alchas et al. |
| 2003/0036752 A1 | 2/2003 | Joye et al. |
| 2003/0109912 A1 | 6/2003 | Joye et al. |
| 2003/0130575 A1 | 7/2003 | Desai |
| 2003/0181896 A1 | 9/2003 | Zvuloni et al. |

(56) References Cited

U.S. PATENT DOCUMENTS

| | | |
|---|---|---|
| 2003/0195436 A1 | 10/2003 | Van Bladel et al. |
| 2003/0220635 A1 | 11/2003 | Knowlton et al. |
| 2003/0220674 A1 | 11/2003 | Anderson et al. |
| 2004/0024391 A1 | 2/2004 | Cytron et al. |
| 2004/0082943 A1 | 4/2004 | Littrup et al. |
| 2004/0092875 A1 | 5/2004 | Kochamba |
| 2004/0122482 A1 | 6/2004 | Tung et al. |
| 2004/0143252 A1 | 7/2004 | Hurst |
| 2004/0162551 A1 | 8/2004 | Brown et al. |
| 2004/0167505 A1 | 8/2004 | Joye et al. |
| 2004/0191229 A1 | 9/2004 | Link et al. |
| 2004/0204705 A1 | 10/2004 | Lafontaine |
| 2004/0210212 A1 | 10/2004 | Maurice |
| 2004/0215178 A1 | 10/2004 | Maurice |
| 2004/0215294 A1 | 10/2004 | Littrup et al. |
| 2004/0215295 A1 | 10/2004 | Littrup et al. |
| 2004/0220497 A1 | 11/2004 | Findlay et al. |
| 2004/0220648 A1 | 11/2004 | Carroll |
| 2004/0225276 A1 | 11/2004 | Burgess |
| 2004/0243116 A1 | 12/2004 | Joye et al. |
| 2004/0267248 A1 | 12/2004 | Duong et al. |
| 2004/0267257 A1 | 12/2004 | Bourne et al. |
| 2005/0004563 A1 | 1/2005 | Racz et al. |
| 2005/0177147 A1 | 8/2005 | Vancelette et al. |
| 2005/0177148 A1 | 8/2005 | van der Walt et al. |
| 2005/0182394 A1 | 8/2005 | Spero et al. |
| 2005/0203505 A1 | 9/2005 | Megerman et al. |
| 2005/0203593 A1 | 9/2005 | Shanks et al. |
| 2005/0209565 A1 | 9/2005 | Yuzhakov et al. |
| 2005/0209587 A1 | 9/2005 | Joye et al. |
| 2005/0224086 A1 | 10/2005 | Nahon |
| 2005/0228288 A1 | 10/2005 | Hurst |
| 2005/0251103 A1 | 11/2005 | Steffen et al. |
| 2005/0261753 A1 | 11/2005 | Littrup et al. |
| 2005/0276759 A1 | 12/2005 | Roser et al. |
| 2005/0281530 A1 | 12/2005 | Rizoiu et al. |
| 2005/0283148 A1 | 12/2005 | Janssen et al. |
| 2006/0009712 A1 | 1/2006 | Van Bladel et al. |
| 2006/0015092 A1 | 1/2006 | Joye et al. |
| 2006/0069385 A1 | 3/2006 | Lafontaine et al. |
| 2006/0079914 A1 | 4/2006 | Modesitt et al. |
| 2006/0084962 A1 | 4/2006 | Joye et al. |
| 2006/0089688 A1 | 4/2006 | Panescu |
| 2006/0111732 A1 | 5/2006 | Gibbens et al. |
| 2006/0129142 A1 | 6/2006 | Reynolds |
| 2006/0142785 A1 | 6/2006 | Modesitt et al. |
| 2006/0173469 A1 | 8/2006 | Klein et al. |
| 2006/0189968 A1 | 8/2006 | Howlett et al. |
| 2006/0190035 A1 | 8/2006 | Hushka et al. |
| 2006/0200117 A1 | 9/2006 | Hermans |
| 2006/0212028 A1 | 9/2006 | Joye et al. |
| 2006/0212048 A1 | 9/2006 | Crainich |
| 2006/0223052 A1 | 10/2006 | MacDonald et al. |
| 2006/0224149 A1 | 10/2006 | Hillely |
| 2006/0258951 A1 | 11/2006 | Bleich et al. |
| 2007/0060921 A1 | 3/2007 | Janssen et al. |
| 2007/0088217 A1 | 4/2007 | Babaev |
| 2007/0129714 A1 | 6/2007 | Elkins et al. |
| 2007/0156125 A1 | 7/2007 | DeLonzor |
| 2007/0161975 A1 | 7/2007 | Goulko |
| 2007/0167943 A1 | 7/2007 | Janssen et al. |
| 2007/0167959 A1 | 7/2007 | Modesitt et al. |
| 2007/0179509 A1 | 8/2007 | Nagata et al. |
| 2007/0198071 A1 | 8/2007 | Ting et al. |
| 2007/0255362 A1 | 11/2007 | Levinson et al. |
| 2007/0270925 A1 | 11/2007 | Levinson |
| 2008/0051775 A1 | 2/2008 | Evans |
| 2008/0051776 A1 | 2/2008 | Bliweis et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0154254 A1 | 6/2008 | Burger et al. |
| 2008/0183164 A1 | 7/2008 | Elkins et al. |
| 2008/0200910 A1 | 8/2008 | Burger et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0171203 A1 | 7/2009 | Avital et al. |
| 2009/0171334 A1 | 7/2009 | Elkins et al. |
| 2009/0248001 A1 | 10/2009 | Burger et al. |
| 2009/0264876 A1 | 10/2009 | Roy et al. |
| 2009/0299357 A1 | 12/2009 | Zhou |
| 2009/0306639 A1 | 12/2009 | Nevo et al. |
| 2011/0144631 A1 | 6/2011 | Elkins et al. |
| 2012/0065629 A1 | 3/2012 | Elkins et al. |
| 2012/0089211 A1 | 4/2012 | Curtis et al. |
| 2012/0108953 A1 | 5/2012 | Markowitz et al. |
| 2012/0265187 A1 | 10/2012 | Palmer, III et al. |
| 2012/0265278 A1* | 10/2012 | Fourkas ................ A61B 18/02 607/105 |
| 2013/0184696 A1 | 7/2013 | Fourkas et al. |
| 2013/0190745 A1 | 7/2013 | Fourkas et al. |
| 2013/0324990 A1 | 12/2013 | Burger et al. |
| 2014/0249519 A1 | 9/2014 | Burger et al. |

FOREIGN PATENT DOCUMENTS

| | | |
|---|---|---|
| EP | 777123 | 6/1997 |
| EP | 955012 | 11/1999 |
| EP | 1074273 | 2/2001 |
| EP | 1377327 | 1/2004 |
| EP | 1862125 | 12/2007 |
| GB | 1360353 | 7/1974 |
| GB | 1402632 | 8/1975 |
| JP | 60013111 | 1/1985 |
| JP | 04357945 | 12/1992 |
| JP | 0538347 | 2/1993 |
| JP | 10014656 | 1/1998 |
| JP | 2001178737 | 7/2001 |
| JP | 2005080988 | 5/2005 |
| JP | 2006130055 | 5/2006 |
| JP | 2008515469 | 5/2008 |
| RU | 2254060 | 6/2005 |
| WO | 9749344 | 12/1997 |
| WO | 0197702 | 12/2001 |
| WO | 0202026 | 1/2002 |
| WO | 02092153 | 11/2002 |
| WO | 2004039440 | 5/2004 |
| WO | 2004045434 | 6/2004 |
| WO | 2004089460 | 10/2004 |
| WO | 2005000106 | 1/2005 |
| WO | 2005079321 | 9/2005 |
| WO | 2005096979 | 10/2005 |
| WO | 2006012128 | 2/2006 |
| WO | 2006023348 | 3/2006 |
| WO | 2006044727 | 4/2006 |
| WO | 2006062788 | 6/2006 |
| WO | 2006125835 | 11/2006 |
| WO | 2006127467 | 11/2006 |
| WO | 2007025106 | 3/2007 |
| WO | 2007037326 | 4/2007 |
| WO | 2007089603 | 8/2007 |
| WO | 2007129121 | 11/2007 |
| WO | 2007135629 | 11/2007 |
| WO | 2008021920 | 2/2008 |
| WO | 2009026471 | 2/2009 |
| WO | 2010075438 | 7/2010 |
| WO | 2015069792 | 5/2015 |

OTHER PUBLICATIONS

CryoPen, LLC webpage, retrieved from the internet at http://cryopen.com/, 2006-2008, 2 pages.

"Cryoprobe™", One Med Group, LLC, retrieved from the internet at: http://www.onemedgroup.com/ on Feb. 4, 2008, 2 pages.

CyroPen, LLC Press Release, "CryoPen, LLC Launches Revolutionary, State-of-the-Art Medical Device—The Dure of Cryosurgery in a Pend", dated Apr. 27, 2007, retrieved from the internet at: http://cryopen.com/press.htm, 3 pages.

(56) References Cited

OTHER PUBLICATIONS

Metrum CryoFlex, Cryoablation in Pain Management Brochure, 2012, 5 pages.
Metrum CryoFlex, Cryosurgery Probes and Accessories Catalogue, 2009, 25 pages.
"Wikipedia: Symmetric-key algorithm", Oct. 3, 2005, XP002734369, retrieved from the internet on Feb. 17, 2015; URL:http://en.wikipedia.org/w/index.php?title=Symmetric-key_algorithm&oldid=24675570, 3 pages.
U.S. Appl. No. 61/116,050, filed Nov. 19, 2008, entited "Cryosurgical Safety Valve Arrangement and Methods for Its Use in Cosmetic and Other Treatment" by Timothy Holland et al.
U.S. Appl. No. 61/801,268, filed Mar. 15, 2013, entitled "Cryogenic Blunt Dissection Methods and Devices" by John Allison.
Cryosurgical Concepts, Inc., "CryoProbe™", retrieved from the Internet: http://www.cryo-surgical.com, Feb. 8, 2008, 2 pages.
Dasiou-Plankida , "Fat Injections for Facial Rejuvenation: 17 Years Experience in 1720 Patients", Journal of Cosmetic Dermatology, vol. 2, Issue No. 3-4, Oct. 22, 2004, pp. 119-125.
Foster et al., "Radiofrequency Ablation of Facial Nerve Branches Controlling Glabellar Frowning", Dermatol Surg, vol. 35, Issue No. 12, Dec. 2009, pp. 1908-1917.
Har-Shai et al., "Effect of Skin Surface Temperature on Skin Pigmentation During Contact and Intralesional Cryosurgery of Hypertrophic Scars and Kleoids", Journal of the European Academy of Dermatology and Venereology, vol. 21, Issue No. 2, Feb. 2007, 14 pages.
Magalov et al., "Isothermal Volume Contours Generated in a Freezing Gel by Embedded Cryo-needles with Applications to Cryo-Surgery", Cryobiology, vol. 55, Issue No. 2, Oct. 2007, pp. 127-137.
International Search Report and Written Opinion dated Jan. 23, 2015, from International Application No. PCT/US2014/064163, 14 pages.
Rewcastle et al., "A Model for the Time Dependent Three-Dimensional Thermal Distribution within Iceballs Surrounding Multiple Cryoprobes", Medical Physics, vol. 28, Issue No. 6, Jun. 2001, pp. 1125-1137.
Rutkove, "Effects of Temperature on Neuromuscular Electrophysiology", Muscles and Nerves, vol. 24, Issue No. 7, Jun. 12, 2001, pp. 867-882.
Utley et al., "Radiofrequency Ablation of the Nerve to the Corrugator Muscle for Elimination of Glabellar Furrowing", Archives of Facial Plastic Surgery, vol. 1, Issue No. 1, Jan.-Mar. 1999, pp. 46-48.
Yang et al., "Apoptosis Induced by Cryo-Injury in Human Colorectal Cancer Cells is Associated with Mitochondrial Dysfunction", International Journal of Cancer, vol. 103, Issue No. 3, Jan. 2003, pp. 360-369.

\* cited by examiner

SECURE CRYOSURGICAL TREATMENT SYSTEM

CROSS-REFERENCES TO RELATED APPLICATIONS

This application is a Continuation Application of U.S. patent application Ser. No. 14/534,120 filed Nov. 5, 2014 (Allowed) which claims the benefit of U.S. Provisional Application No. 61/900,345, filed Nov. 5, 2013, both of which are incorporated by reference herein in their entirety.

BACKGROUND OF THE INVENTION

Medical devices can include a handpiece for operational control of a detachable tip used for applying a therapy, such as electrocautery or cryogenic therapy. In many instances, the detachable tip is designed and approved for a single use, or a limited amount of uses, and should be disposed afterwards. For example, a detachable tip can have a very fine cryogenic needle that dulls after use, and thus rendered unable to pierce tissue in an intended manner. In other cases, the detachable tip cannot be safely sterilized after use.

Unfortunately, some users reuse detachable tips in spite of these dangers. This can cause problems such as patient injury or infection. Additionally, fraudsters may produce duplicate tips without authorization. These duplicate tips can be unsafe because of faulty construction or sterilization methods, since manufacture is unregulated. Accordingly, there is a need to address these issues.

BRIEF SUMMARY OF THE INVENTION

Embodiments of the invention can include a therapy system having a disposable device and a durable device. Each device can include a secure microprocessor with applications code and configuration data.

In some embodiments, one secure processor can be located in the handheld/durable device, such a cryogenic therapy device, and the other secure processor can be located in a disposable/consumable device (e.g. a detachable probe with at least one cryogenic needle), which is adapted to receive cryogenic cooling fluid from the handheld device, interface with tissue to provide direct therapy to a patient, and mechanically couple and decouple with the handheld device.

In some embodiments, the handheld device can include a microprocessor control unit (MCU) with software applications code, communication links and related electronic circuitry. The secure processor (HSP) in the handheld device contains custom software and configuration data, and may include one or more X509 digital certificates. The secure processor in the disposable device (DSP) can also contain custom software and configuration data, including one or more ITU-T X509 (ISO/IEC 9594-8) digital certificates. Such configuration data can include a predetermined amount of treatment cycles, treatment cycle parameters, tip identification, and performance test parameters.

In some embodiments, the two secure processors can communicate with one another by way of electronic circuitry of the MCU. Software in the MCU and the secure processors implements communication protocols, including commands and replies. The software contains logic to perform an authentication according to a protocol, such as public key infrastructure (PKI)-based authentication, between the durable and consumable patient treatment devices. This software uses cryptographic techniques to establish trusted identity and secure communication.

In some embodiments, the disposable device can be authenticated using PKI signing challenge methods issued by the HSP. The DSP may refuse a request to provide the application configuration data if authentication has not been completed. This feature, optionally in conjunction with a design in which the handpiece or disposable device requires this external data for operation, provides a way of denying use of the system in cases where trust has not been established that the disposable device is authentic. The authentication method may be extended to two-way authentication. Accordingly, one or more disposable device components authenticate one or more handheld device components in addition to the authentication processes initiated by the one or more durable components. In some embodiments, the disposable device may authenticate the handpiece in a one-way authentication process.

In some embodiments, the authentication method can be extended to cover multiple types of disposable devices (e.g., pain treatment needles, cosmetic needles, etc.). This design alternative could enforce an electronic manifest, configured in the disposable device, which would authenticate the set(s) of disposable devices.

In some embodiments, interprocessor communication devices and protocols may be used including I2C, SPI, serial, or ISO7816.

In some embodiments, the disposable device and handheld device can communicate wirelessly. The use of wireless communication between disposable and durable components will support a product architecture where the components are not directly connected.

In some embodiments, the MCU can connect to a remote authorization service. In this embodiment, the disposable device and/or handpiece is authenticated remotely. The authenticated device can then provide one or more communications channels for one or more disposable components, which in turn are authenticated.

In some embodiments, a network of trust is created across a plurality of durable and disposable components.

Embodiments include a system with a probe having at least one cryogenic treatment applicator and a disposable secure processor (DSP), a handpiece removeably coupled to the probe and configured to provide cryogen coolant from a coolant supply system to the probe, the handpiece having a microprocessor control unit (MCU) and a handpiece authentication processor (HSP).

Embodiments also include a method for operating the system. The method includes detecting connection of the probe to the handpiece and initiating an authentication process between the DSP and HSP using the MCU as a communications router. As a result of the authentication process, determining one of at least two predetermined results, the at least two predetermined results comprising that the probe is authorized and non-authorized.

In some embodiments, the authentication process comprises the HSP requesting a certificate from the DSP.

In some embodiments, the authentication process comprises requesting a certificate from the DSP; validating the certificate; creating a nonce; encrypting the nonce with the public key in the certificate; sending a request to the DSP to decrypt the nonce using a private key; receiving the decrypted nonce from the DSP; and verifying the decrypted nonce.

In some embodiments, the probe is authorized after the DSP completes a signing challenge or non-authorized after the DSP fails the signing challenge.

In some embodiments, the signing challenge comprises the HSP requesting a certificate from the DSP.

In some embodiments, the DSP returns the digital certificate to the HSP as part of the signing challenge.

In some embodiments, the HSP validates the authenticity of the digital certificate by using one or more stored digital certificates issued by an authority.

In some embodiments, the HSP uses a public cryptographic key contained in the certificate provided by the DSP to encrypt a nonce.

In some embodiments, the HSP transmits the nonce to the DSP and requests a decrypted reply.

In some embodiments, the DSP uses a private cryptographic key associated with the public cryptographic key, contained in the digital certificate previously transmitted, to decrypt the encrypted nonce.

In some embodiments, the HSP compares the decrypted nonce with the previously transmitted challenge nonce.

In some embodiments, the probe is authenticated when the HSP successfully matches the sent nonce with the decrypted nonce, or non-authorized if: the decrypted nonce does not match the sent nonce or if the DSP fails to reply to the certificate request or the decrypt request.

In some embodiments, as a result of the authentication process the probe is determined to be authorized.

In some embodiments, the method also includes accessing recorded history settings of the DSP and based on the history settings, determining one of: that the probe is expired and non-expired.

In some embodiments, based on the recorded history settings, the probe is determined to be non-expired.

In some embodiments, as a result that the probe is determined to be non-expired, data is retrieved from the DSP containing procedural instructions for the MCU for operating the probe.

In some embodiments, the data comprises a tip descriptor that includes identification, treatment cycle and system control parameters, and test settings. The tip descriptor is used by the MCU to control the system for testing the probe and performing treatment cycles. The DSP firmware can include one or more X.509 certificates and an expiration descriptor. The expiration descriptor can include a version type, allowed cycles, total minutes of validity from first use, and a list of handpiece types which are compatible with the probe.

In some embodiments, a request is sent to the DSP to check the allowed remaining uses of the probe.

In some embodiments, after receiving the request the DSP determines the remaining allowable uses of the probe and provides the MCU with one of: an indication that the probe has no remaining uses available and an indication that the probe can be used.

In some embodiments, the DSP provides the MCU with the indication that the probe can be used and increments a use-counter of the probe.

In some embodiments, based on the history settings, the probe is determined to be expired.

In some embodiments, as a result of the authentication process the probe is determined to be non-authorized for use.

In some embodiments, a user alert is transmitted using the MCU indicating that the probe is not useable with the handpiece.

In some embodiments, each secure processor includes one or more digital certificates and the authentication process comprises performing a cryptographic signing challenge algorithm.

In some embodiments, communication between the secure processors is encrypted during the authentication process.

In some embodiments, the probe is authorized and as a result the MCU indicates to the user that the system is ready to perform a treatment cycle.

In some embodiments, after the probe is authorized and the user initiates the treatment cycle, the MCU sends the start request to the DSP.

In some embodiments, the DSP processes the treatment start request by determining the remaining authorized uses, decrementing the remaining uses, and returning a reply which indicates either the treatment is authorized or the probe is expired.

In some embodiments, the MCU uses the reply from the DSP to either begin a treatment cycle or indicate to the operator that the probe is expired.

Some embodiments include a cryogenic handpiece operable by a microprocessor control unit. A probe is removeably coupled to the handpiece, configured to receive coolant from the handpiece, and has a processor communicatively coupled to the microprocessor control unit. The processor includes operating instructions for execution by the microprocessor to control metering of the coolant to the probe.

Some embodiments include a cryogenic probe with a body having at least one cryogenic treatment applicator fluidly connectable to a separate coolant supply device for providing power, data, and/or coolant to the at least one cryogenic treatment applicator. The cryogenic probe includes an integrated circuit storing a tip descriptor In some embodiments, the integrated circuit is a processor.

In some embodiments, the integrated circuit comprises memory for storing the tip descriptor.

In some embodiments, the tip descriptor includes a protocol for timing opening and closing of the controllable valve.

In some embodiments, the body comprises a heater and wherein the tip descriptor includes heater control parameters.

In some embodiments, the tip descriptor includes a target heater temperature.

In some embodiments, the tip descriptor includes test parameters.

In some embodiments, the tip descriptor includes expiration information.

In some embodiments, the tip descriptor comprises instructional parameters for operating the separate coolant supply device.

In some embodiments, the at least one cryogenic treatment applicator comprises a sharpened or round needle Some embodiments include a kit of cryogenic probes with a plurality of cryogenic probes, each cryogenic probe having a body with at least one cryogenic treatment applicator with connections for coolant, power, and data to a separate device for providing coolant, power, and data to the at least one cryogenic treatment applicator. In some embodiments, at least one of the cryogenic probes includes a secure processor comprising memory having instructional parameters for operating coolant supply device with the remaining plurality. In other embodiments, each cryogenic probe can share the same type of treatment applicator configuration, but different instructional parameters.

In some embodiments, a treatment system and method implement different types of probes. These probes are different only with respect to the tip descriptors stored within. Accordingly, a first type of probe can have a specific needle configuration, while the second type of probe shares the same needle configuration. The different tip descriptors, however, contain or identify different types of treatment protocols. For example, the first type of probe is indicated for use on a specific nerve, or particular location within a nerve cluster, requiring a certain cooling curve (temperature vs. time). While the second type of probe is indicated for use on a different nerve, or a different location within the same nerve cluster, requiring a different cooling curve (e.g., colder, less cold, shorter dwell time, etc.).

Some embodiments include a method for cryogenically treating tissue. In the method, a connection is detected of a first type of probe having a first processor to a handpiece having a master control unit (MCU). The handpiece is compatible with a plurality of different types of probes. The first type of probe has at least one cryogenic treatment applicator, and is fluidly coupled to a closed coolant supply system within the handpiece via the connection. A communication process is then initiated between the first processor and the MCU, during which the first processor provides a first type of tip descriptor to the MCU. As a result of the communication process, a first type of treatment protocol is initiated based on the first type of tip descriptor. Some embodiments also include a system for cryogenically treating tissue. The system includes a first type of probe having a first processor and memory storing a first type of tip descriptor. The first type of probe has at least one cryogenic treatment applicator. A handpiece has a master control unit (MCU) and is compatible with a plurality of different types of probes. The first type of probe is fluidly couplable to a closed coolant supply system within the handpiece. The first processor is configured to communicate the first type of tip descriptor to the MCU. The MCU is configured to implement a first type of treatment protocol based on the first type of tip descriptor.

In some embodiments, the first type of treatment protocol is provided by the tip descriptor.

In some embodiments, the treatment protocol is retrieved from memory of the handpiece by the MCU based on identification of the tip descriptor.

In some embodiments, the plurality of different types of probes share the same type of cryogenic treatment applicator configuration.

In some embodiments, the first type of treatment protocol is provided by the first type of tip descriptor.

Some embodiments include a system for cryogenically treating tissue. The system includes a first type of probe having a first processor and first memory storing a first type of tip descriptor. The first type of probe has at least one of cryogenic treatment applicator configuration. The system also includes a second type of probe having a second processor and second memory storing a second type of tip descriptor. The second type of probe shares the same type of cryogenic treatment applicator configuration as the first type of probe. The system also includes a handpiece having a master control unit (MCU). The handpiece is compatible with a plurality of different types of probes. The first and second type of probe are each fluidly couplable in sequence to a closed coolant supply system within the handpiece. The first processor is configured to communicate the first type of tip descriptor to the MCU, and the second processor is configured to communicate the second type of tip descriptor to the MCU. The MCU is configured to implement a first type of treatment protocol based on the first type of tip descriptor, and a second type of treatment protocol based on the second type of tip descriptor. In some embodiments, the first type of treatment protocol relates to a first type of nerve, while the second type of treatment protocol relates to a second type of nerve.

Some embodiments include a method for cryogenically treating tissue. In the method, a first connection is detected of a first type of probe having a first processor to a handpiece having a master control unit (MCU). The handpiece is compatible with a plurality of different types of probes. The first type of probe has at least one cryogenic treatment applicator. The first type of probe is fluidly coupled to a closed coolant supply system within the handpiece via the first connection. A first communication process is imitated between the first processor and the MCU, in which the first processor provides a tip descriptor to the MCU, with the tip descriptor being specific to the first type of probe. As a result of the first communication process, a first type of treatment protocol is initiated based on the first type of tip descriptor. A second connection is detected of a second type of probe, having a second processor, to the handpiece after the first type of probe is decoupled from the handpiece. The second type of probe shares the same type of cryogenic treatment applicator configuration as the first type of probe. The second type of probe is fluidly coupled to the closed coolant supply system within the handpiece via the second connection. A second communication process is initiated between the second processor and the MCU, during which the second processor provides a second type of tip descriptor to the MCU. As a result of the second communication process, a second type of treatment protocol is implemented based on the second type of tip descriptor. The second type of treatment protocol is different from the first type of treatment protocol. In some embodiments, the first type of treatment protocol relates to a first type of nerve or a particular nerve location, while the second type of treatment protocol relates to a second type of nerve or a different nerve location.

DETAILED DESCRIPTION OF THE INVENTION

The present invention provides secured medical devices, systems, and methods. Embodiments of the invention will facilitate safe remodeling of target tissues disposed at and below the skin by providing a secure system that prevents unauthorized use of expired, counterfeit or otherwise unallowed probes.

Among the most immediate applications of related devices may be the amelioration of lines and wrinkles, particularly by treating motor nerves to prevent muscular contractions that are associated with these cosmetic defects so as to improve an appearance of the patient. Additional applications include the treatment of pain in which sensory nerves are treated to prevent the sensation of pain at a particular portion of the body. Additional description of cryogenic cooling for treatment of defects may be found in commonly assigned U.S. Pat. No. 7,713,266 entitled "Subdermal Cryogenic Remodeling of Muscle, Nerves, Connective Tissue, and/or Adipose Tissue (Fat)", U.S. Pat. No. 7,850,683 entitled "Subdermal Cryogenic Remodeling of Muscles, Nerves, Connective Tissue, and/or Adipose Tissue (Fat)", and U.S. patent application Ser. No. 13/325,004, entitled "Method for Reducing Hyperdynamic Facial Wrinkles", U.S. Pub. No. 2009/0248001 entitled "Pain Management Using Cryogenic Remodeling" the full disclosures of which are each incorporated by reference.

Figure 1A:
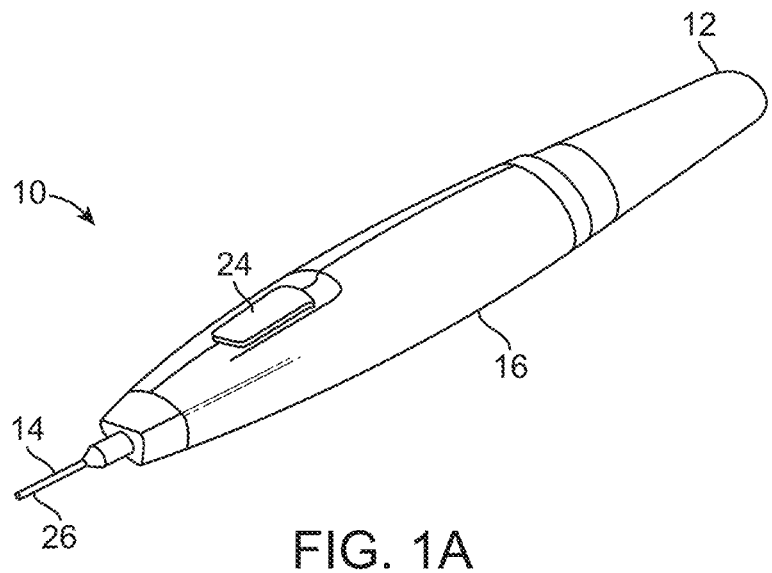
FIG. 1A is a perspective view of a security enabled subdermal cryogenic system, according to some embodiments.
Figure 1B:
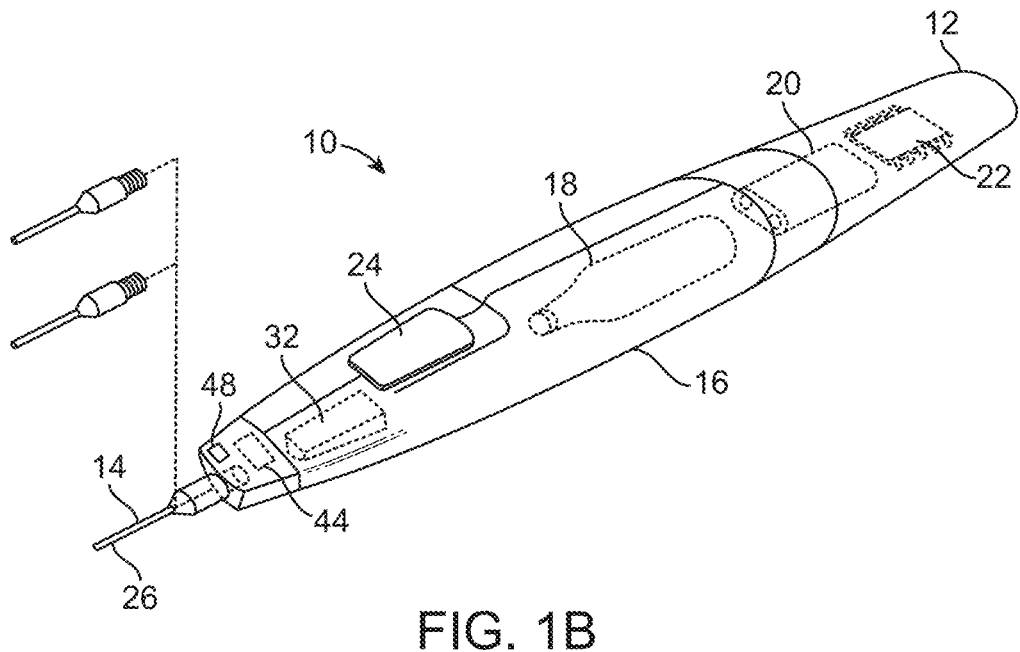
FIG. 1B is a partially transparent perspective view of the cryogenic system of FIG. 1A, showing additional internal components of the cryogenic remodeling system and schematically illustrating secured replacement treatment needles for use with the disposable probe, according to some embodiments.

Referring now to FIGS. 1A and 1B, a system for cryogenic remodeling here comprises a hand held device generally having a proximal end 12 and a distal end 14. A handpiece body or handpiece 16 has a size and ergonomic shape suitable for being grasped and supported in a surgeon's hand or other system operator. As can be seen most clearly in FIG. 1B, a cryogenic cooling fluid supply 18, a supply valve 32 and electrical power source 20 are found within a handpiece 16, along with a circuit having a microprocessor control unit (MCU) 22 that typically comprises a processor for controlling cooling applied by self-contained system 10 in response to actuation of an input 24. Alternatively, electrical power can be applied through a cord from a remote power source. The power source 20 also supplies power to heater element 44 in order to heat the proximal region of the probe 26 thereby helping to prevent unwanted skin damage, and a temperature sensor 48 adjacent the proximal region of the probe 26 helps monitor probe temperature. When actuated, the supply valve 32 controls the flow of cryogenic cooling fluid from the cooling fluid supply 18.

A handpiece secure processor (HSP) 23 (schematically shown in FIG. 2A) is electrically connected to the MCU 22. A secure processor, also known in the art as a secure cryptoprocessor, is a dedicated computer on a chip or microprocessor for carrying out cryptographic operations and storing data. A secure processor is embedded in packaging with multiple physical security measures that provide the secure processor with tamper resistance.

Extending distally from the distal end 14 of the handpiece 16 is a detachable cryogenic cooling probe 26. The probe 26 is coupled to a cooling fluid path extending from a cooling fluid source 18, with the exemplary probe comprising a tubular body receiving at least a portion of the cooling fluid from the cooling fluid source therein. The exemplary probe 26 can include a 27 g needle having a proximal end that is axially sealed. It should be understood that any reference to "needle" herein is meant in a generic sense and refers to any cryogenic treatment applicator and e.g. can comprise an elongated shape, such as a sharpened needle usable for piercing tissue or a rounded or blunted needle that is separately introduced into tissue (e.g. via a cannula) and used for blunt probing/dissection of tissue. The probe 26 may have an axial length between the distal end 14 of the handpiece 16 and the distal end of the needle of between about 0.5 mm and 10 cm. Generally, probe 26 will comprise a 16 g or smaller size needle, often comprising a 20 g needle or smaller, typically comprising a 22, 25, 26, 27, 28, 29, or 30 g or smaller needle.

In some embodiments, probe 26 may comprise two or more needles arranged in a linear array, such as those disclosed in previously incorporated U.S. Pat. No. 7,850,683. Another exemplary embodiment of a probe having multiple probe configurations allow the cryogenic treatment to be applied to a larger or more specific treatment area. Other needle configurations that facilitate controlling the depth of needle penetration and insulated needle embodiments are disclosed in commonly assigned U.S. Patent Publication No. 2008/0200910 entitled "Replaceable and/or Easily Removable Needle Systems for Dermal and Transdermal Cryogenic Remodeling," and U.S. Provisional Patent Application No. 61/801,268 entitled "Cryogenic Blunt Dissection Methods and Devices," the entire contents of which are incorporated by reference. Multiple needle arrays may also be arrayed in alternative configurations such as a triangular or square array. Arrays may be designed to treat a particular region of tissue, or to provide a uniform treatment within a particular region, or both.

The probe 26 is releasably coupled with the handpiece 16 so that it may be replaced after use with a new probe (as indicated by the dotted line in FIG. 1B) or with another probe having a different configuration. In exemplary embodiments, the probe 16 may be threaded into the body, it may be press fit into an aperture in the body or it may have a quick disconnect such as a detent mechanism for engaging the probe with the body. A quick disconnect with a check valve is advantageous since it permits decoupling of the probe from the body at any time without excessive coolant discharge. This can be a useful safety feature in the event that the device fails in operation (e.g. valve failure), allowing an operator to disengage the probe from a patient's tissue without exposing the patient to coolant as the system depressurizes. This feature is also advantageous because it allows an operator to easily exchange an expired or dulled needle with a new needle in the middle of a treatment. One of skill in the art will appreciate that other coupling mechanisms may be used.

In addition to the collant connection, the brobe/handpiece connection provides electrical connections for power, sensor readings, and data communications. These electrical connections may take the form of mechanical contacts such as pin and socket connectors or spring contact probes (commonly referred to as pogo pins) and connection pads.

Addressing some of the components within the handpiece 16, the exemplary cooling fluid supply 18 comprises a canister, sometimes referred to herein as a cartridge, containing a liquid under pressure, with the liquid preferably having a boiling temperature of less than 37° C. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between a canister 18 and the probe 26, or along the cooling fluid path after the probe so as to limit coolant flow thereby regulating the temperature, treatment time, rate of temperature change, or other cooling characteristics. The valve 32 will often be powered electrically via power source 20, per the direction of MCU 22, but may at least in part be manually powered. The exemplary power source 20 comprises a rechargeable or single-use battery. Additional details about valve 32 are disclosed below and further disclosure on the power source 20 may be found in commonly assigned Int'l Pub. No. WO 2010/075438 entitled "Integrated Cryosurgical Probe Package with Fluid Reservoir and Limited Electrical Power Source," the entire contents of which is incorporated by reference. The exemplary cooling fluid supply 18 comprises a single-use canister. Advantageously, the canister and cooling fluid therein may be stored and/or used at (or even above) room temperature.

The MCU 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, the MCU 22 may be integrated on a single processor board and may run a single program or may make use of a plurality of boards running a number of different program modules in a wide variety of alternative distributed data processing or code architectures.

Figure 2A:
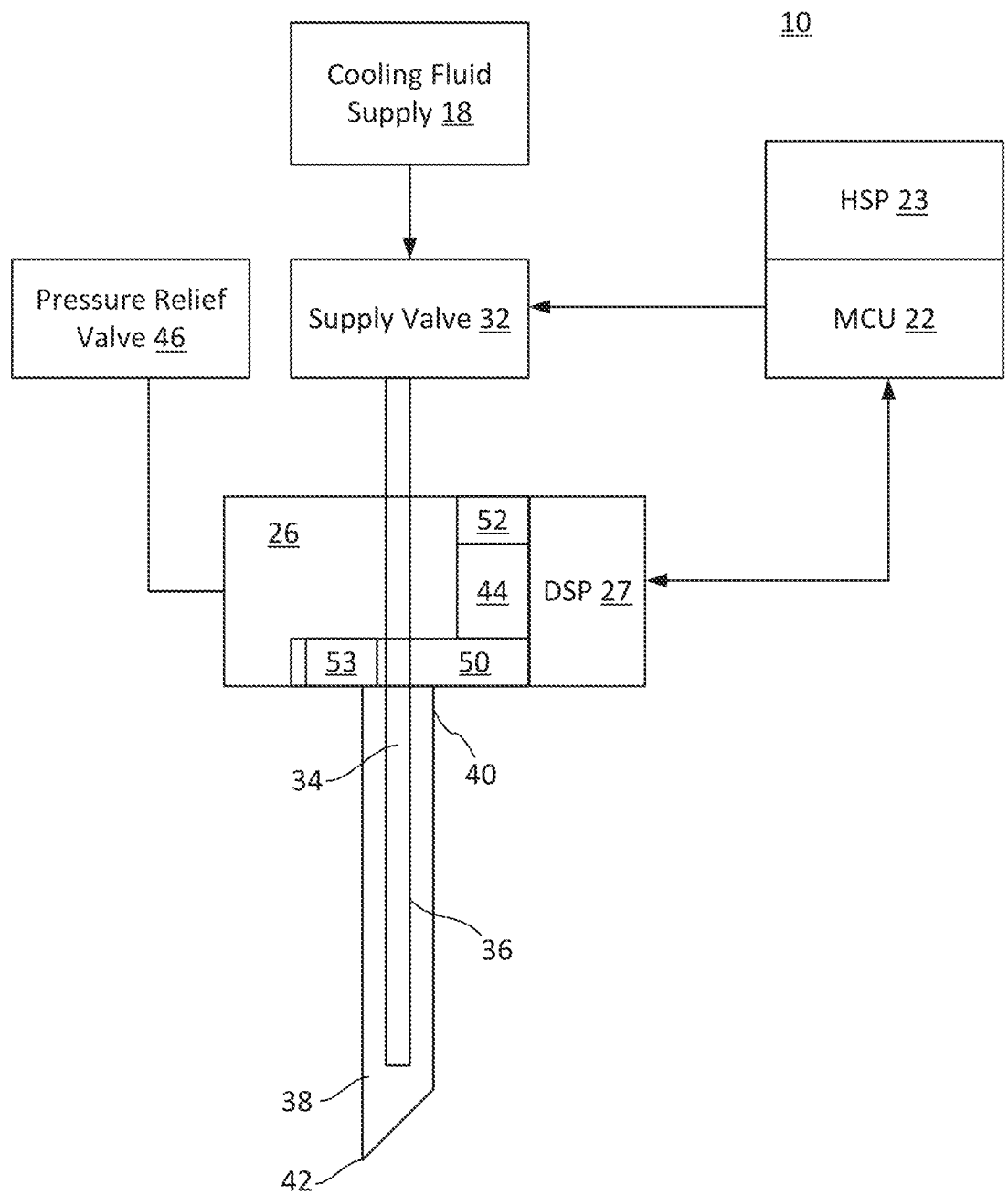
FIG. 2A schematically illustrates components that may be included in the treatment system of FIG. 1A, according to some embodiments.

Referring now to FIG. 2A, the flow of cryogenic cooling fluid from fluid supply 18 is controlled by a supply valve 32. The supply valve 32 may comprise an electrically actuated solenoid valve, a motor actuated valve or the like operating in response to control signals from the MCU 22 to implement an authorized treatment algorithm. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the MCU 22 in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pub. No. 2008/0200910.

Still referring to FIG. 2A, an optional coolant supply heater (not shown), thermally coupled to the Cooling Fluid Supply may be controlled by the MCU 22 according to an authorized algorithm to heat cooling fluid supply 18 so that heated cooling fluid flows through valve 32 and through a lumen 34 of a cooling fluid supply tube 36. Supply tube 36 is, at least in part, disposed within a closed lumen 38 of probe 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Previously incorporated U.S. Patent Publication No. 2008/0200910 discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. The MCU 22 can control the probe heater 44 according to an authorized treatment algorithm to heat the proximal region of the needle 26 in order to prevent unwanted skin damage in this area, as discussed in greater detail below. Controlling a pressure of the gas/liquid mixture within lumen 38 substantially controls the temperature within lumen 38, and hence the treatment temperature range of the tissue. A relatively simple mechanical pressure relief valve 53 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050 previously incorporated herein by reference. Thus, the relief valve allows better temperature control in the needle, minimizing transient temperatures. Further details on exhaust volume are disclosed in previously incorporated U.S. Pat. Pub. No. 2008/0200910.

A temperature sensor 52 (e.g., thermistor, thermocouple) can also be thermally coupled to a thermally responsive element 50 that receives heat from the heater 44, and communicatively coupled to the MCU 22. The MCU 22 can be configured according to an authorized treatment algorithm to receive temperature information of the thermally responsive element 50 via the temperature sensor 52 in order to provide the heater 44 with enough power to maintain the thermally responsive element 50 at a particular temperature. The probe 26 also includes a secure processor referred to herein as the disposable secure processor (DSP) 27 that communicates with the MCU 22 and HSP 23.

The MCU 22 can be further configured according to an authorized treatment algorithm to monitor power draw from the heater 44 in order to characterize tissue type, perform device diagnostics, and/or provide feedback for a tissue treatment algorithm. This can be advantageous over monitoring temperature since power draw from the heater 44 can vary greatly while temperature of the thermally responsive element 50 remains relatively stable.

Alternative methods to inhibit excessively low transient temperatures at the beginning of a refrigeration cycle may be employed by the MCU 22 according to an authorized treatment algorithm, instead of or together with the limiting of the exhaust volume. For example, the supply valve might be cycled on and off by the MCU 22, with a timing sequence that would limit the cooling fluid flowing so that only vaporized gas reached the needle lumen (or a sufficiently limited amount of liquid to avoid excessive dropping of the needle lumen temperature). Analytical models that may be used to estimate cooling flows are described in greater detail in U.S. Pub. No. 2008/0154254, previously incorporated by reference. The application of a treatment algorithm may include the control of multiple parameters such as temperature, time, cycling, pulsing, and ramp rates for cooling or thawing of treatment areas. In parallel with the treatment algorithm, one or more power monitoring algorithms can be implemented. Examples of such treatment and power monitoring algorithms are disclosed in U.S. patent application Ser. No. 13/741,360, which is incorporated by reference.

Figure 2B:
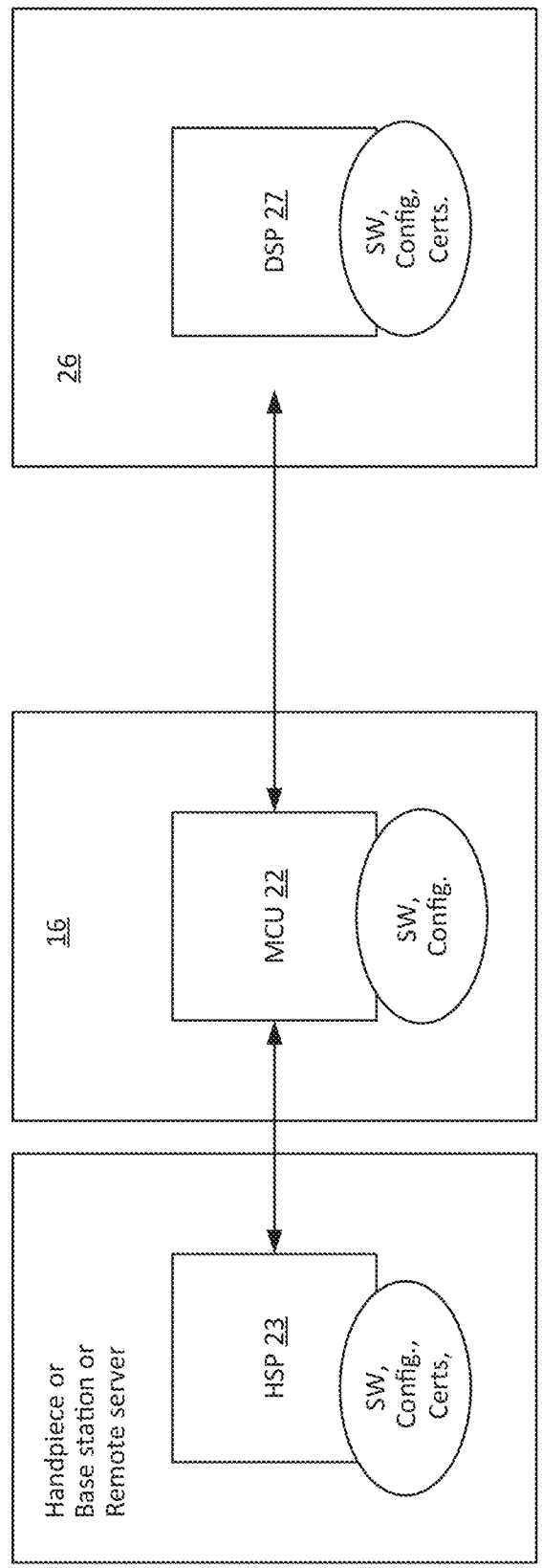
FIG. 2B illustrates a security communication architecture that may be included in the treatment system of FIG. 1A, according to some embodiments.

FIG. 2B shows a portion of FIG. 2A to illustrate the security communication architecture between the handpiece 16 and the probe 26. The MCU 22 serves as a communications router between the HSP 23 and the DSP 27. The MCU 22 contains software applications code, communication links and related electronic circuitry. The HSP 23 can contain memory with custom software and configuration data, and may include one or more digital certificates (e.g., X509 certificates). The probe secure processor DSP 27 can also contain memory with custom software and a tip descriptor, which includes configuration and/or identification data, and in some embodiments can include one or more digital certificates (e.g., X509 certificates). The tip descriptor can be stored as a binary large object (blob) or similar data structure that includes operational instructions for the MCU 22. These instructions conform to the type of probe 26 being used, since different types of probes (needle count, size, application) require different metering of cryogenic fluid and in some cases heater power. Such instructions can include a predetermined amount of treatment cycles, treatment cycle parameters, treatment control parameters, tip identification, probe/handpiece compatibility settings and performance test parameters. Accordingly, without this data the MCU 22 cannot operate the cryogenic system when connected with the probe 26. This is advantageous, since it can prevent fraudsters from producing effective copies since the instructions can be difficult to procure.

The two secure processors can communicate with one another by way of electronic circuitry and software of the MCU 22. Software in the MCU 22 and the secure processors implements communication protocols, including command and reply. The software contains logic to perform authentication (e.g., PKI-based) between the disposable and reusable patient treatment devices. This software uses cryptographic techniques to establish trusted identity and secure communication. Interprocessor communication devices and protocols may be used that include, e.g., I2C, SPI, serial, or ISO7816. In some embodiments, the probe 26 and the handpiece 16 can communicate wirelessly. The use of wireless communication between disposable and durable components may support a product architecture where the components are not directly connected. For example, in some cases, the handpiece 16 can rest on a recharging base station when not in use, and the HSP 23 may reside within the base station, while the MCU 22 resides in the handpiece 16. Accordingly, the HSP 23 is not limited to be being physically located within a "handpiece." In addition, while the term "durable" as used herein is commonly associated with a handheld device, the term can include handheld devices dock or other remotely accessed accessories. The charging base may in turn serve as a gateway to local and wide-area network services. The services may include customer support, product security, inventory management, treatment monitor, training, and brand extension content.

The probe 26 can be authenticated using PKI signing challenge methods by the HSP 23. In some embodiments, the DSP can authenticate the HSP. The DSP 27 may refuse a request to provide the application configuration data if authentication has not been completed. This feature, optionally in conjunction with a feature that requires the probe 26 and handpiece 16 to use external data for operation, provides a way of denying use of the cryogenic system in cases where trust has not been established that the probe 26 is authentic and not expired. In some embodiments, the MCU 22 can send the request to start a cooling cycle to HSP 23, which then uses encrypted communications to forward the request to DSP 27 only if the one or both of the processors have been authenticated.

The authentication method between the HSP 23 and DSP 27 may include two-way authentication. That is, the DSP 27 will require authentication of the HSP 23 in addition to the HSP 23 requiring authentication of the DSP 27 before allowing further communication or before providing the tip descriptor. Accordingly, one or more probe components may authenticate one or more handpiece components, in addition to the authentication processes initiated by the one or more handpiece components.

In some embodiments, the authentication method can be extended to cover multiple types of probes (e.g., pain treatment needles, cosmetic needles, etc.). This design alternative could enforce an electronic manifest, configured in the disposable device, which would authenticate the set(s) of disposable devices. For example, if a certain procedure required a probe kit for sequential probe use, e.g., a first type of probe and a second type of probe (or more) or a plurality of identical probes, then the first probe would provide authentication for remaining probe(s).

In some embodiments, the MCU 22 can connect to a remote authorization service. For example the HSP 23 may be located in a remote server that the MCU 22 remotely communicates with. In this embodiment the disposable device is authenticated remotely. The authenticated disposable device can then provide one or more communications channels for one or more disposable components, which in turn are authenticated. In some embodiments, the HSP 23, or both the HSP 23 and the DSP 27, can require authentication by a remote PKI server prior to further operation. This authentication may include comparing the digital certificates stored in the secure processors to a list of revoked x509 certificates issued by a trusted Certificate Authority. This would allow a remote capability to disable a device.

Figure 3A:
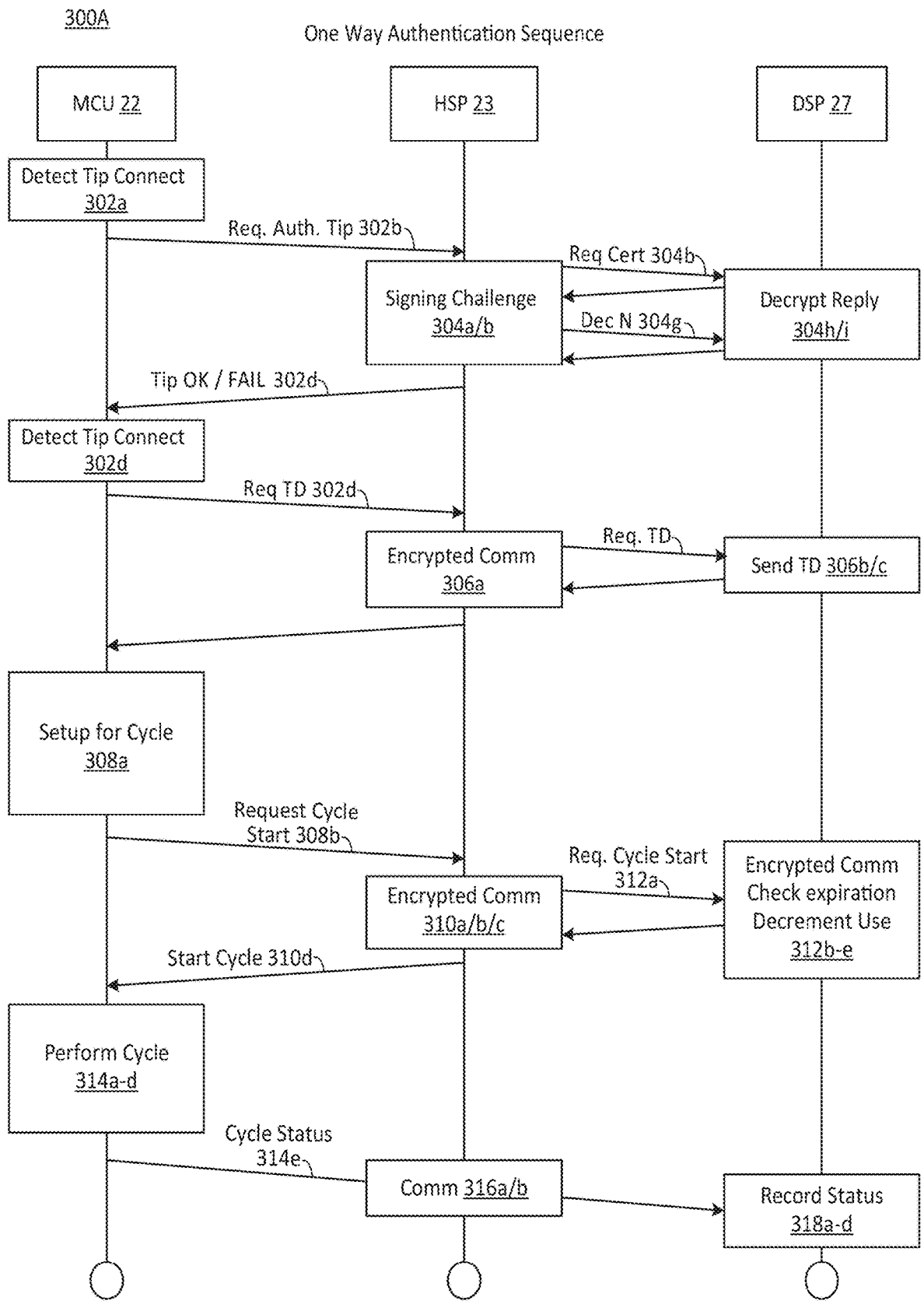
FIG. 3A illustrates a sequence diagram for an operational method for operating the treatment system of FIG. 1A, according to some embodiments.
Figure 3B:
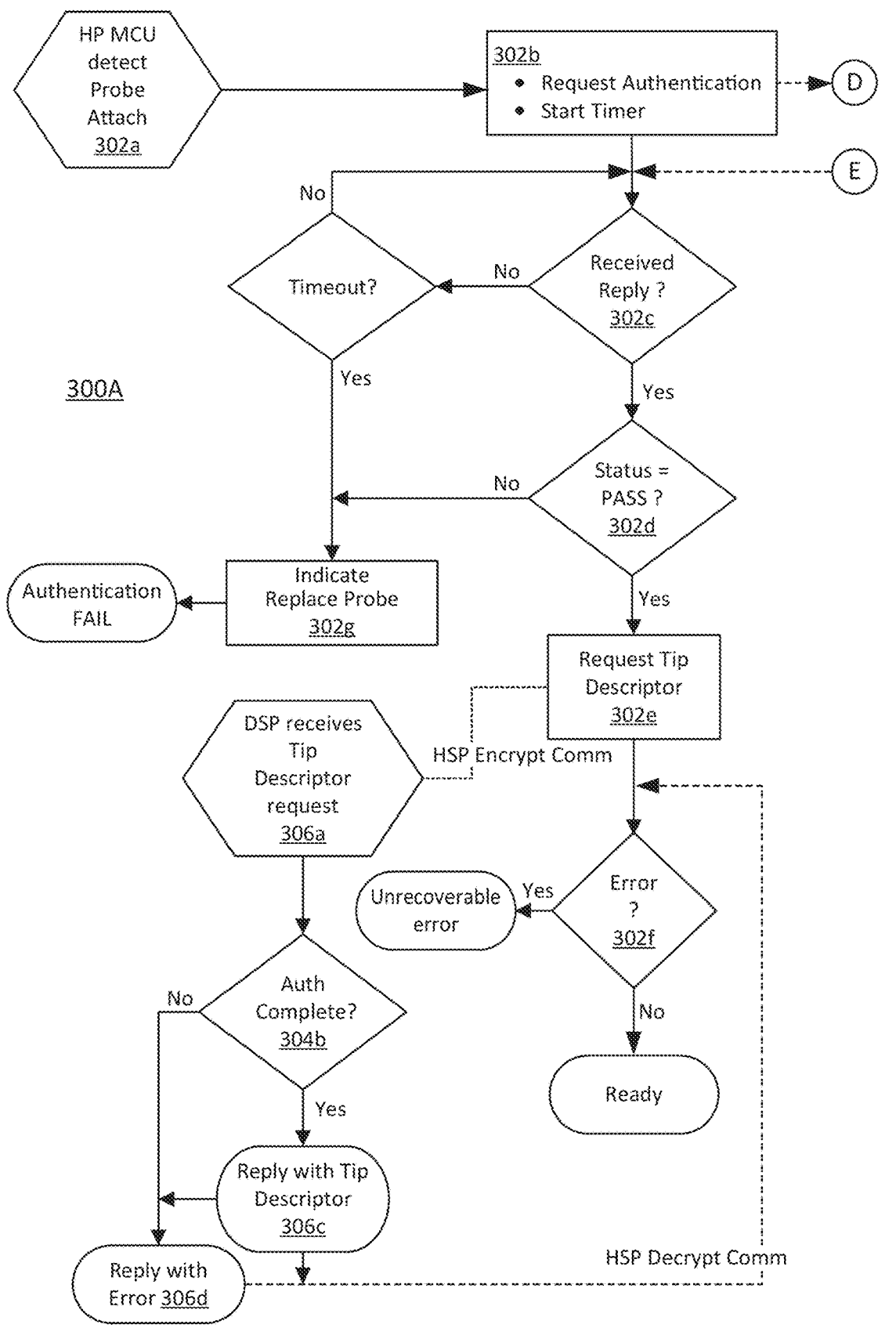
FIGS. 3B and 3C illustrates a flow chart for an operational method for operating the treatment system of FIG. 1A, according to some embodiments.
Figure 3B:
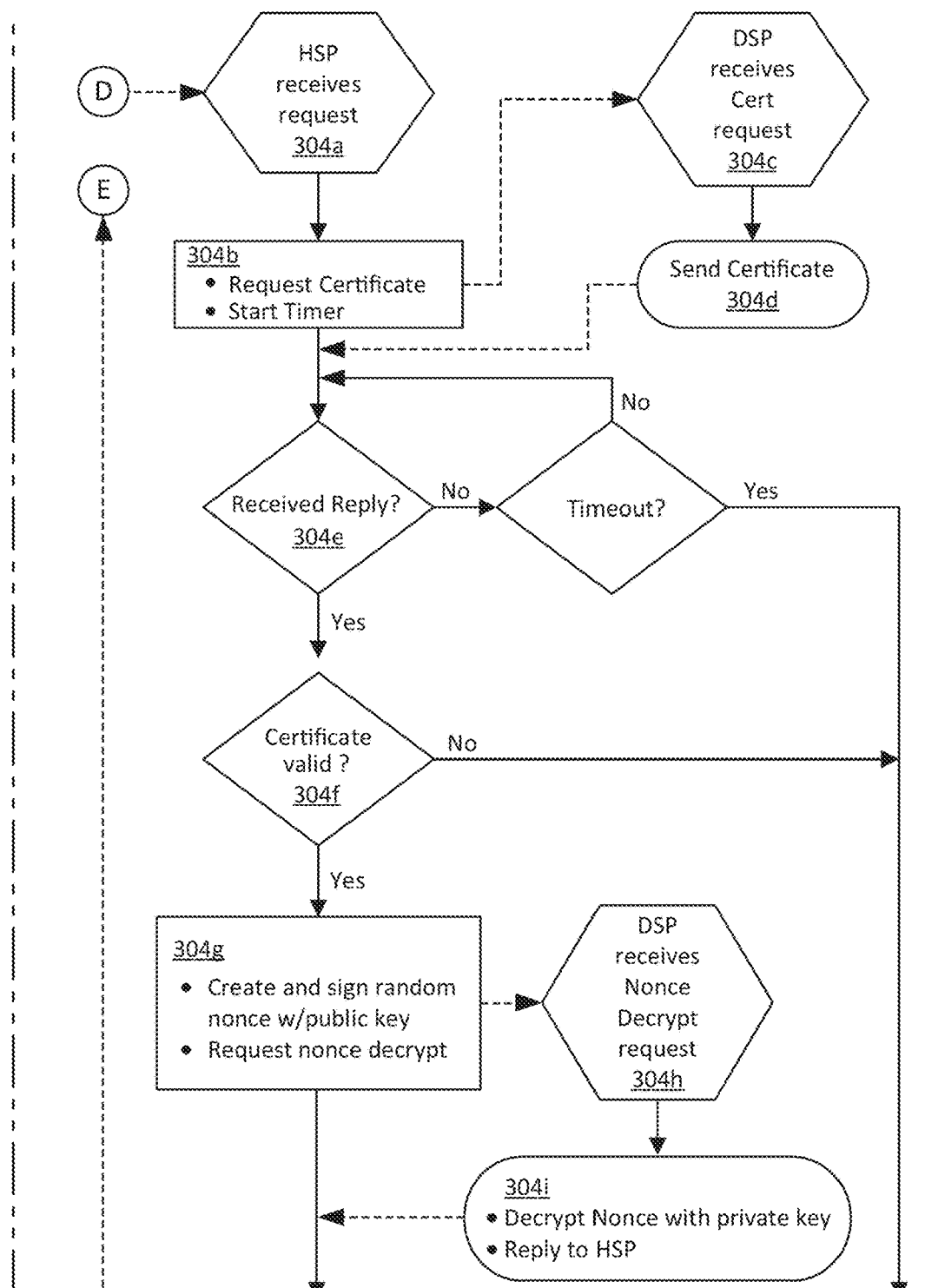
Figure 3B:
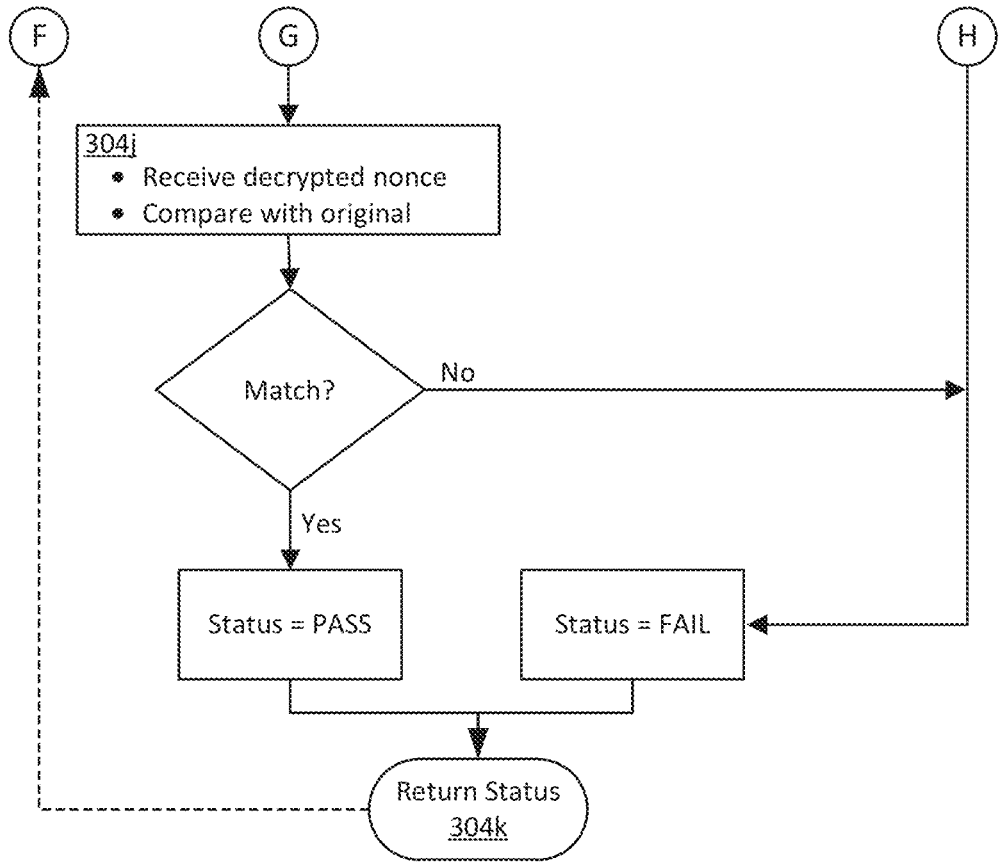
Figure 3C:
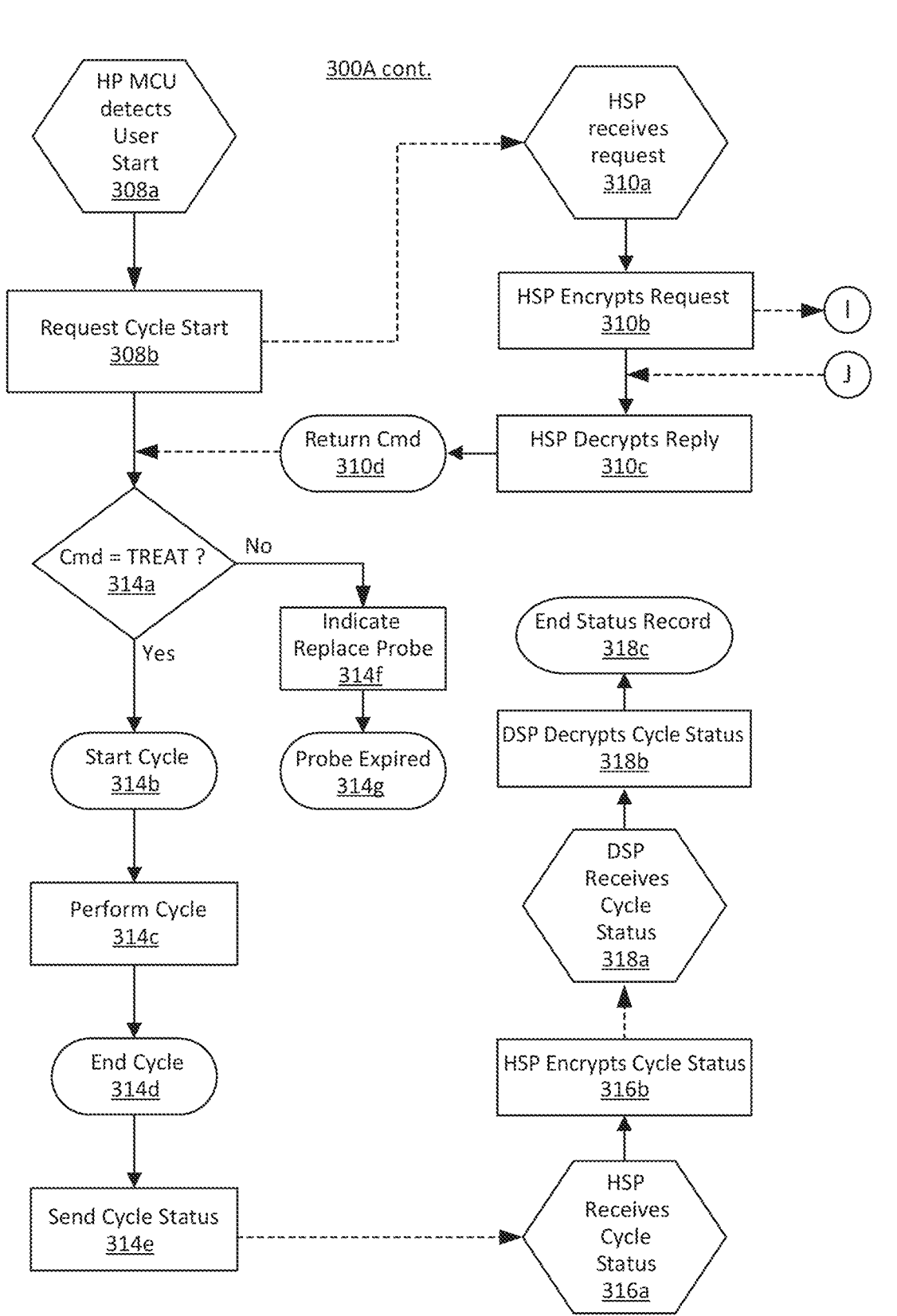
Figure 3C:
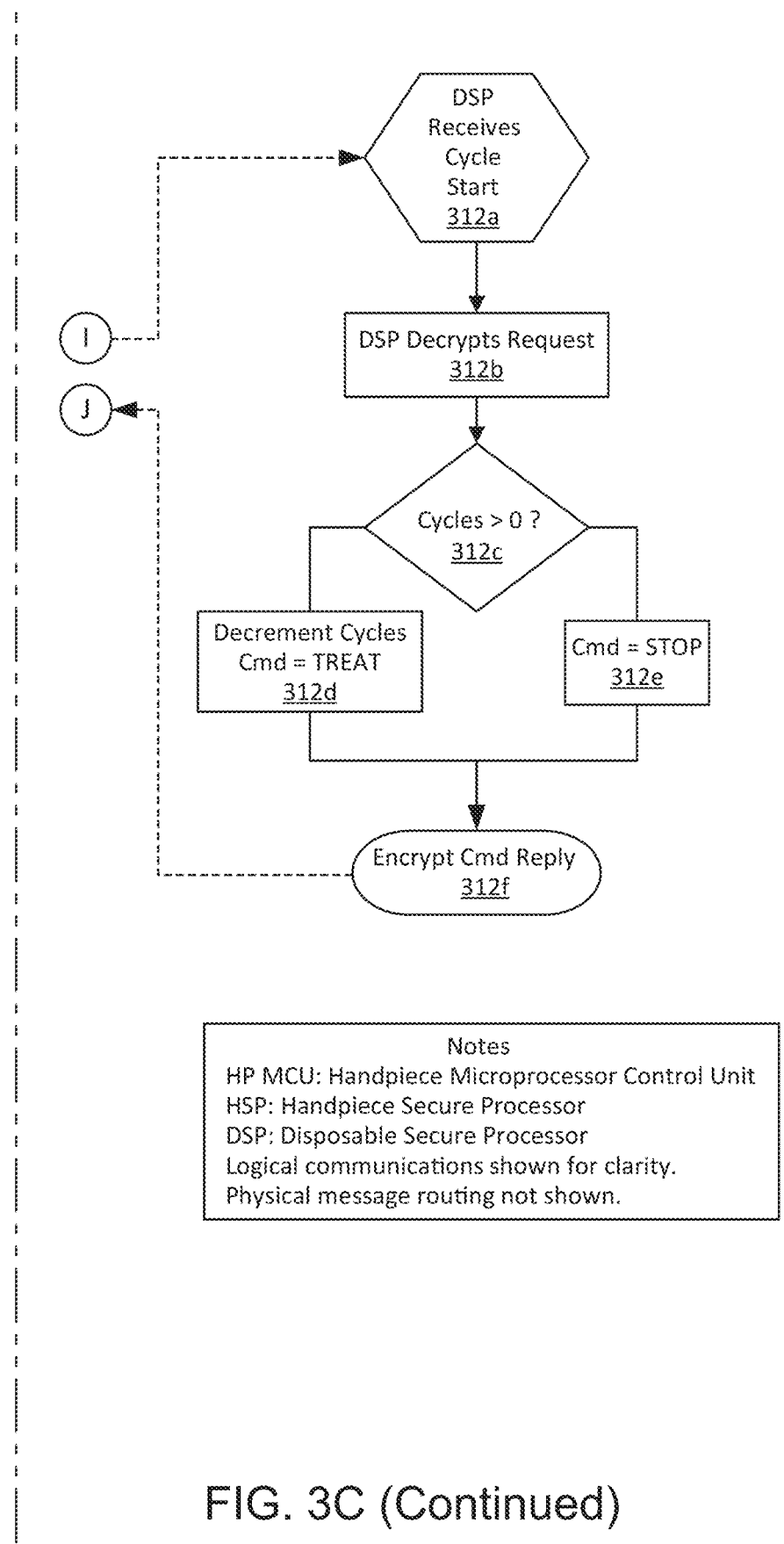

FIGS. 3A-3C illustrate a logical method 300A of authentication between the HSP 23 and DSP 27, using the MCU 22 as a communications router. FIG. 3A is a sequence chart of the method 300A. FIG. 3B primarily shows the authentication portion of the method 300A by way of a flow diagram, while FIG. 3C includes a post authentication treatment cycle continuing from FIG. 3B.

With attention primarily to FIG. 3B, at operation 302a the MCU 22 detects that the probe 26 has been connected to the handpiece 16 and accordingly initiates a probe connection protocol. Accordingly, at operation 302b the MCU 22 sends a request the HSP 23 to authenticate the probe 26 and also initiates a first timer to start a predetermined count-down to receive a reply from the HSP 23.

At operation 304a the HSP 23 at operation 304a receives the authentication request from the MCU 22, and at operation 304b issues an authentication challenge to the DSP 27 and initiates a second timer to start a predetermined count-down to receive a reply from the DSP 27. This challenge may include requesting a certificate from the DSP 27.

At operation 304c the DSP 27 receives the authentication challenge from the HSP 23. At operation 304d, the DSP 27 answers the challenge, e.g., the DSP 27 will return an X.509 compliant certificate.

At operation 304e the HSP 23 receives the certificate from the DSP 27 assuming the second timer has not run out, which would result in a authentication failure. At operation 304f the HSP 23 can verify the authenticity of the certificate using one or more stored digital certificates issued by an authorized authority. Non-verification results in an authentication failure.

Assuming the certificate is verified, at operation 304g the HSP 23 can create and encrypt a nonce (i.e., number used once) using a public key, and then request the DSP 27 to decrypt the nonce, which can only be done using a private key. At operation 304h the DSP 27 receives the decryption request and encrypted nonce from the HSP 23. At operation 304i the DSP 27 decrypts the encrypted nonce using the private key from the verified certificate and sends the decrypted nonce back to the HSP 23 for verification by the HSP 23 at operation 304j. If the DSP 27 correctly decrypts the encrypted nonce and returns it to the HSP 23, and if the HSP verifies the decrypted nonce against the original within the time limit of the second timer, then the tip is authenticated. However, if the DSP 27 does not decrypt the nonce, then the tip is not authenticated. As a result, at operation 304k the HSP 23 communicates the authentication result (pass/fail) to the MCU 22.

At operation 302c the MCU 22 determines if the authentication result is received within the time limit of the first timer. If the MCU 22 has not received a reply within the time limit of the first timer, the process stops. At operation 302d the MCU 22 determines if the authentication result has passed or failed. If authentication fails, the MCU 22 refuses to operate with the probe 26 and the process stops. In either case of a time run-out or authentication failure, the MCU 22 provides an indicator (e.g., flashing light) to the user that the probe 26 is unusable at operation 302g. At this point, probe authentication is complete. However, communication between the DSP 27 and MCU 22 and or HSP 23 is still required for further operation.

If authentication is established, the probe connection detection protocol continues at operation 302e, where the MCU 22 requests system parameters to operate the probe, i.e., the tip descriptor. Accordingly, the HSP 23 sends an encrypted communication to the DSP 27 requesting the tip descriptor. At operation 306a the DSP 27 receives the request for the tip descriptor. At operation 306b the DSP checks whether the authentication protocol is completed, if so, the DSP 27 sends the tip descriptor to the MCU 22 at operation 306c. If the authentication protocol has not been completed, then the DSP 27 sends an error message to the MCU 22 at operation 306d. The HSP 23 then decrypts the tip descriptor for the MCU 22. The MCU 22 can then provide an indicator (e.g., steady light) to the user that the probe is useable.

With attention now primarily to FIGS. 3A and 3C, the method 300A continues to operation 308a in which the MCU 22 is ready to begin coolant flow and/or heater functions according to particular instructions received in the tip descriptor. These instructions are based on the particular type of needle configuration and/or intended therapy procedure for the probe 26. In some cases, the probe 26 is reusable, but only for a particular number of instances and/or a predetermined amount of time after first use. The DSP 27 is configured to record historical use using a counter and clock. Hence, at operation 308b the MCU 22 is required to request an initiation signal of the treatment cycle from the DSP 27, via an encrypted communication by the HSP 23 at operation 310a. The encrypted communication is send to the DSP 27 at operation 310b.

At operation 312a/b the DSP 27 receives and decrypts the request from the HSP 23. At operations 312c the DSP 27 determines whether there are greater than zero cycles remaining on the counter. If there are cycles remaining, at operation 312d the DSP 27 decrements the counter and issues a command to treat. If no cycles remain, then at operation 312e the DSP issues a command to halt use. At operation 312f, the resulting command is encrypted by the DSP 27 and sent to the HSP 23, which at operations 310c/310d is decrypted and sent to the HSP 22.

If the count and/or date indicates to the DSP 27 that the probe 26 is expired, then at operations 314f/g the MCU 22 can then provide an indicator (e.g., flashing light) to the user that the probe 26 is unusable. Optionally, the MCU 22 may essentially break itself (unrecoverable error) to avoid any attempted fraudulent use, such that the MCU 22 can only be used further if reset in a specific manner. Conversely, if the treat command is received, the MCU 22 may begin a treatment cycle, which occurs at operation 314b. The MCU 22 can then provide an indicator (e.g. steady light) to the user that the probe 26 is useable. During the treatment cycle, at operation 314c, the MCU 22 fluidly connects the probe 26 to the cooling fluid supply 18 by operation of the valve 32 and provides power to the heater 44 if present, according to the parameters received in the tip descriptor.

After the treatment cycle is performed, at operation 314e the MCU 22 sends a status indication of the cycle status to the DSP 27 by way of the HSP 23, which encrypts and sends the status indication at operations 316a/b. For example, cycle status can indicate whether the cycle was successful or unsuccessful. The cycle status can be decrypted and recorded by the DSP 27 at operations 318a/b. Based on this, the DSP 27 may prevent future use if the status indicates that the probe 26 is faulty. Status may also include sensor data useful for troubleshooting procedure issues.

Figure 3D:
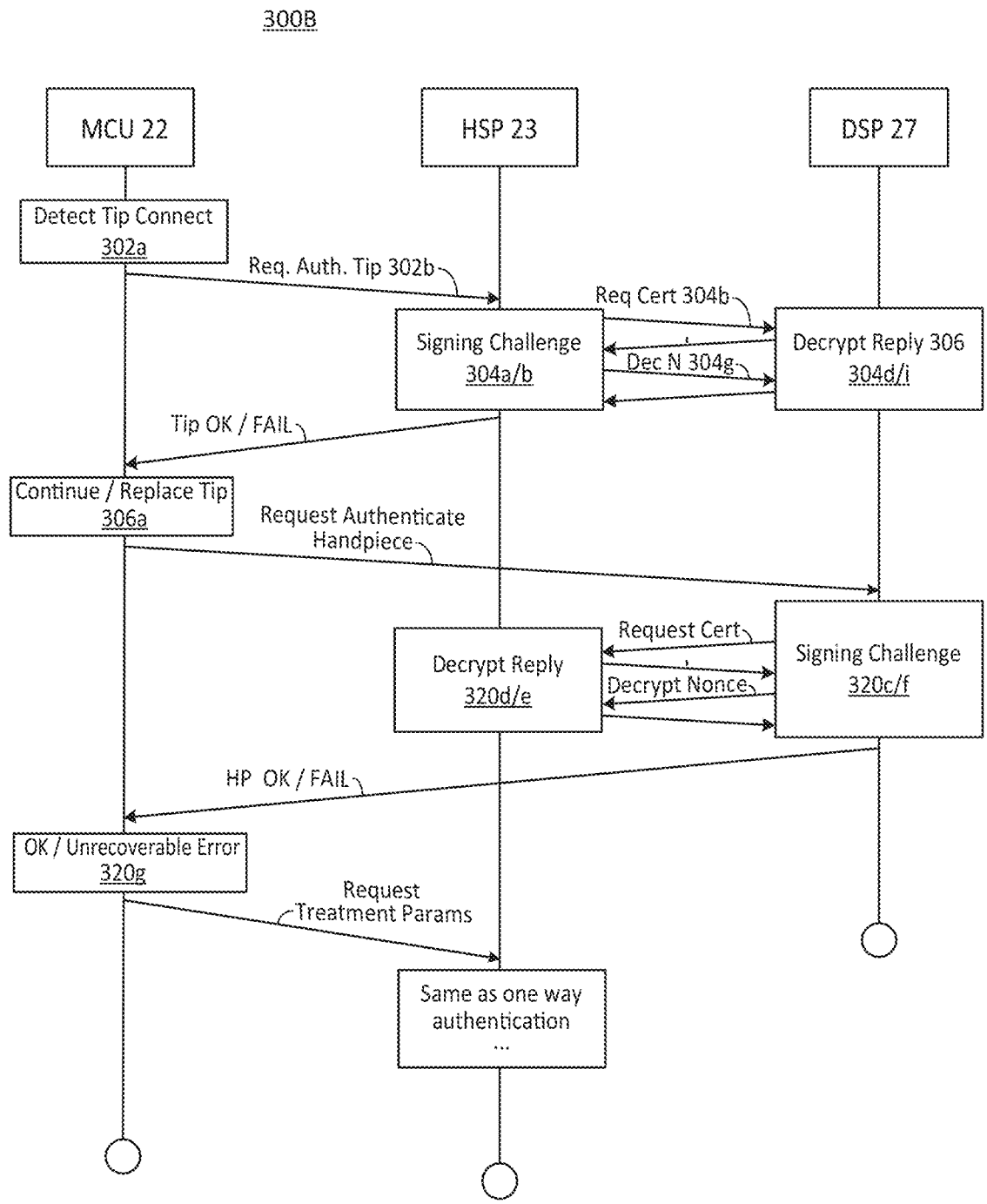
FIG. 3D illustrates a sequence diagram for an operational method for operating the treatment system of FIG. 1A, according to some embodiments.
Figure 3E:
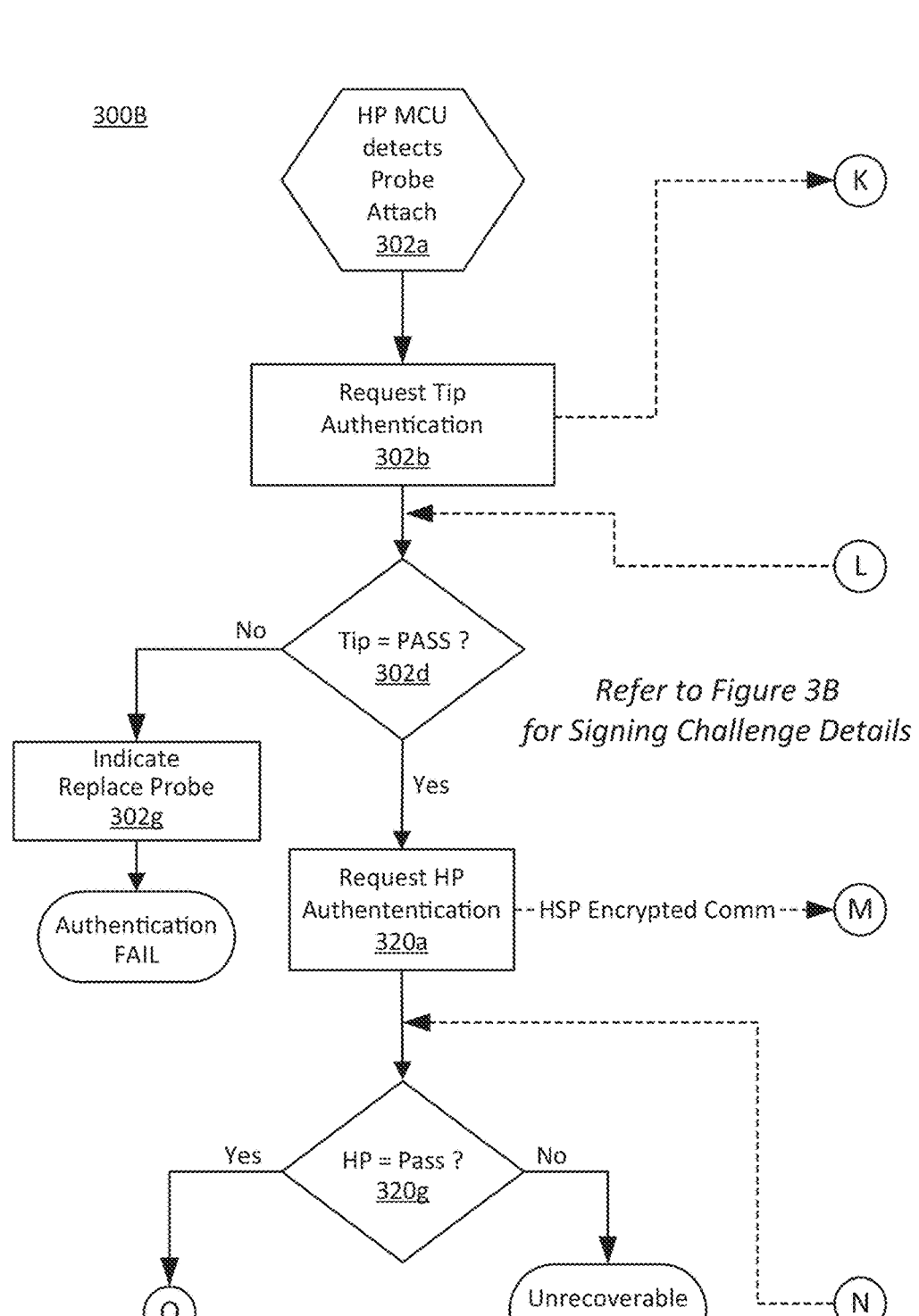
FIG. 3E illustrates a flow chart for an operational method for operating the treatment system of FIG. 1A, according to some embodiments.
Figure 3E:
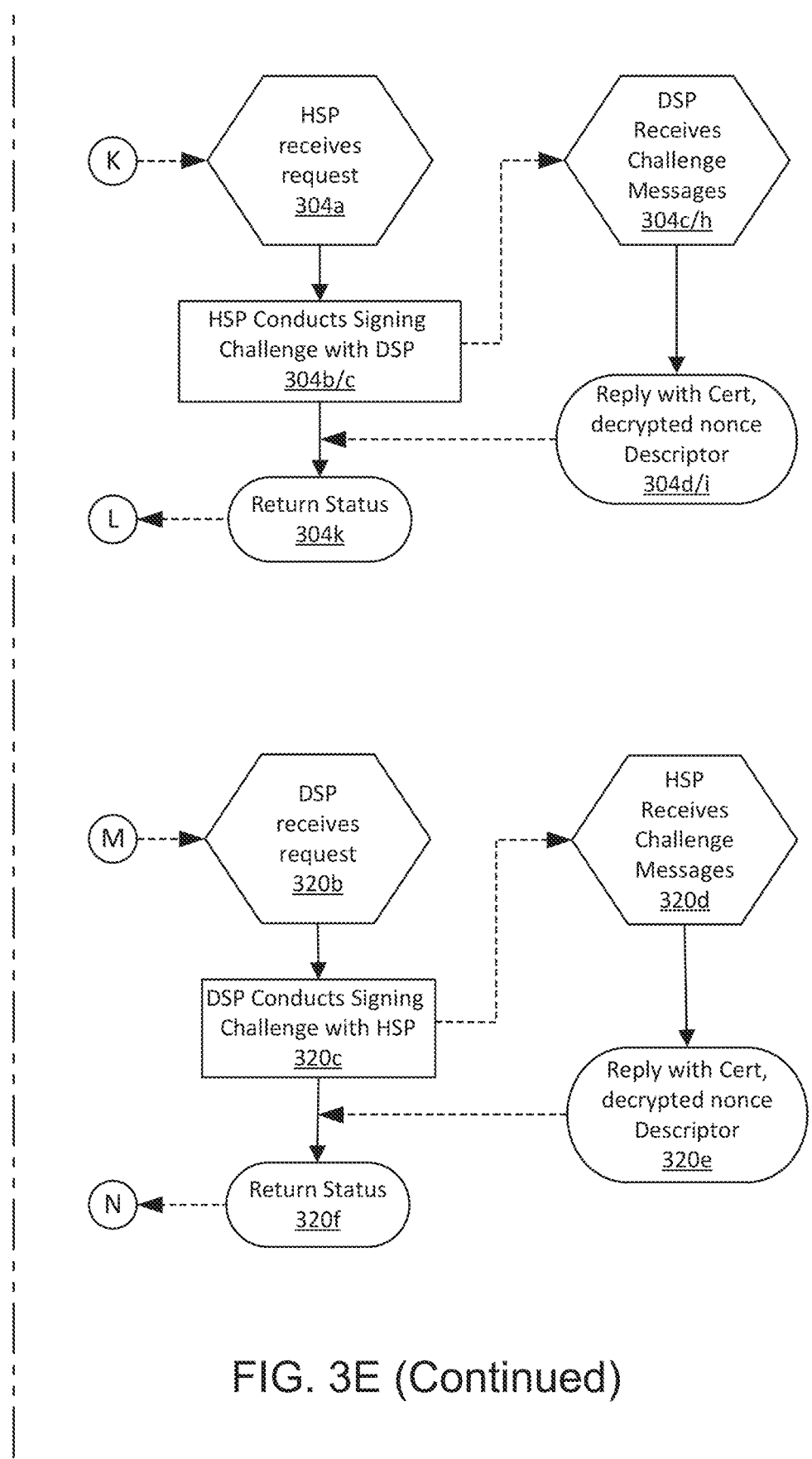
Figure 3E:
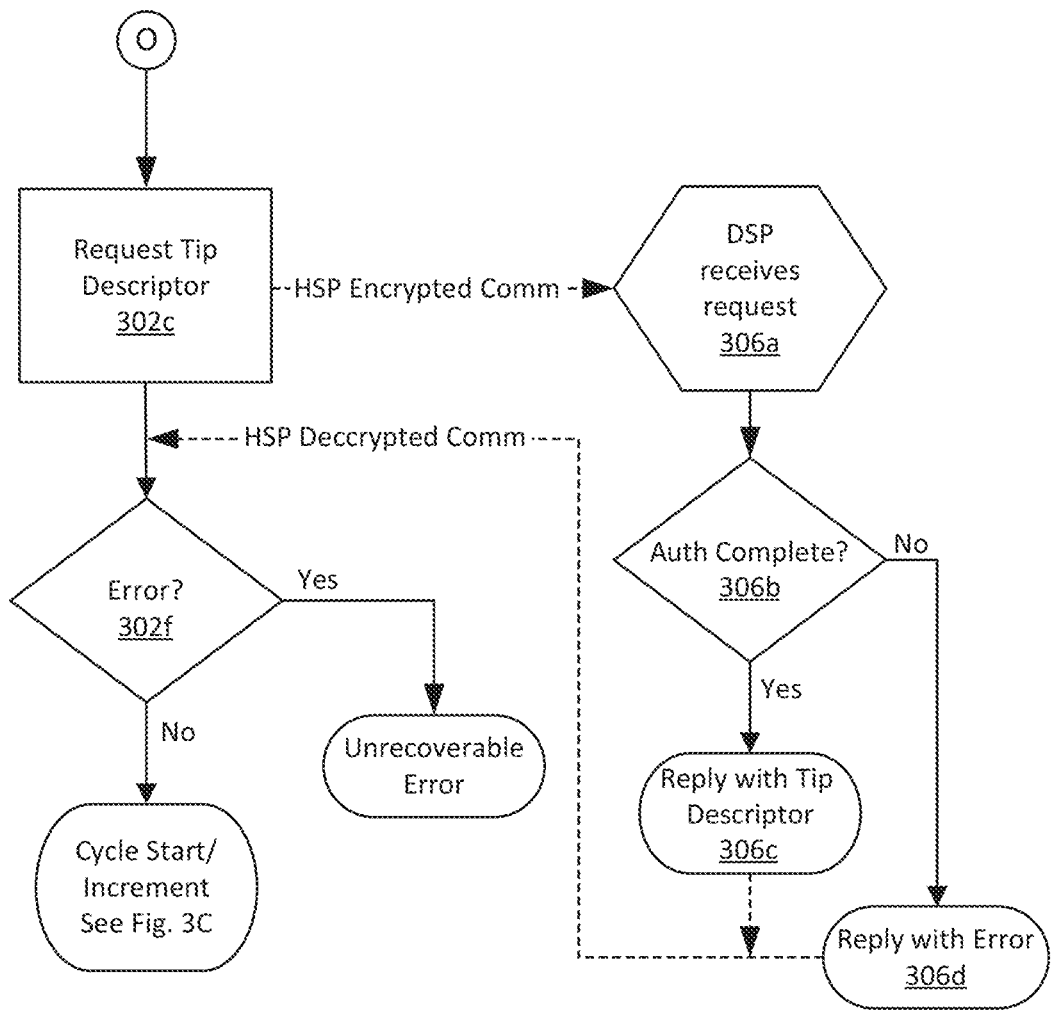

A mutual authentication method 300B is shown in FIG. 3D and FIG. 3E. The method is largely the same as depicted in FIGS. 3A-3C, with the added procedure to authenticate the handpiece. Hence, the description above applies to most of FIGS. 3D and 3E.

Upon completion of tip authentication, at operations 320a to 320b the MCU 22 may send a message to the DSP 27 requesting that the DSP 27 authenticate the handpiece. This may be accomplished by the DSP 27 performing a signing challenge with the HSP 23 (i.e., certificate verification and nonce decryption) in operations 320c to 320g, as described above. Two-way authentication may also optimize traffic by interleaving the two authentication sequences. For example, the MCU 22 may send authentication requests to the HSP 23 and the DSP 27. The certificate request can be accompanied by the challenger's certificate.

Figure 4:
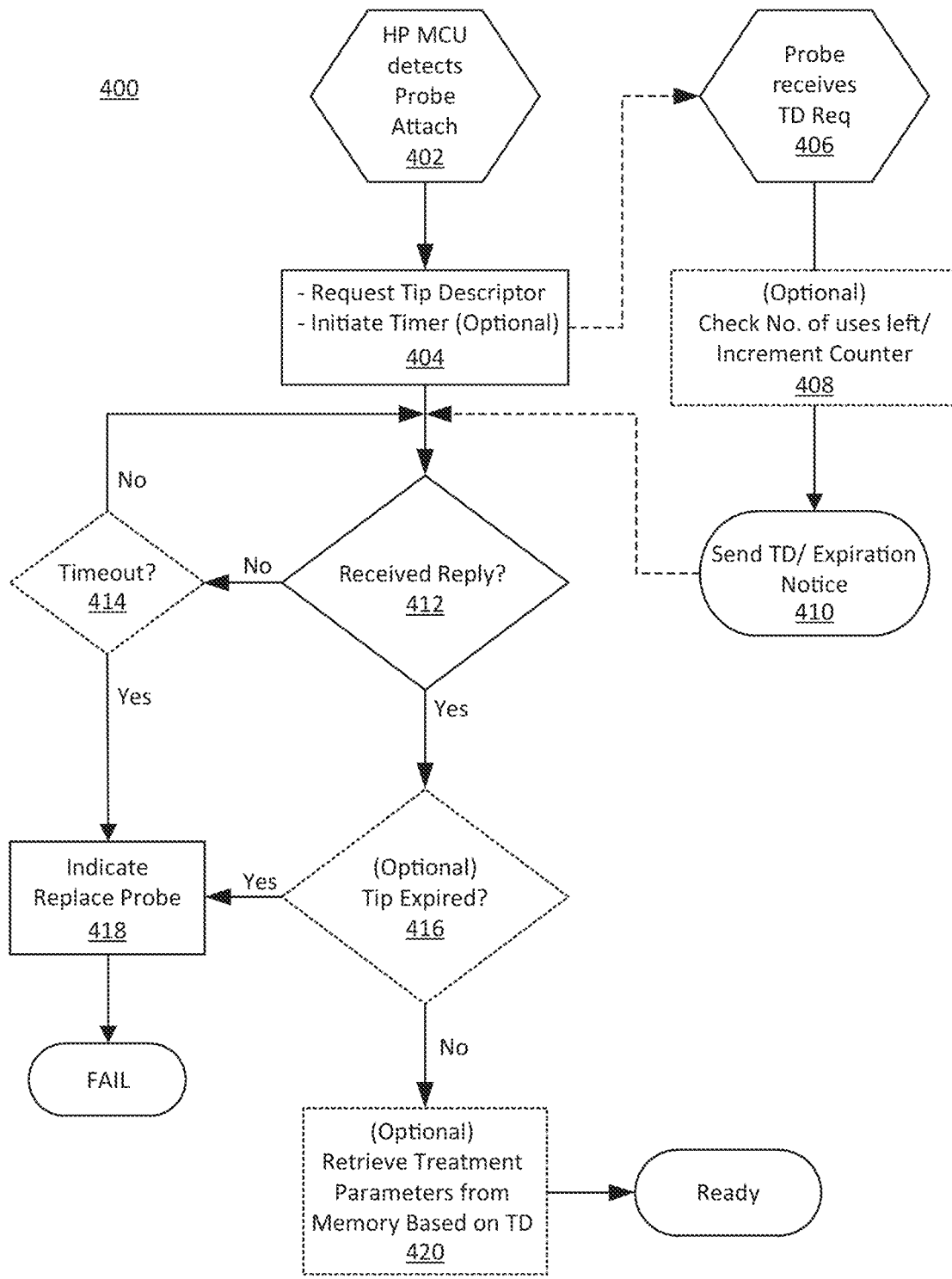
FIG. 4 illustrates a flow chart for an operational method for operating the treatment system of FIG. 1A, according to some embodiments.

FIG. 4 shows a simplified authentication method 400. In some embodiments, secure authorization is not necessary, accordingly, the MCU 22 and the DSP 27, which may be a non-secure processor in this case, can communicate directly without the need for encryption. At operation 402 the handpiece MCU 22 detects connection of the probe, and accordingly at operation 404 sends a request for a tip descriptor and optionally initiates a timer.

At operation 406 the DSP 27 receives the request for the tip descriptor. The DSP 27 may optionally check if any cycles remain for use and if so decrement a counter at operation 408. At operation 410 the DSP 27 sends the tip descriptor or expiration indicator back to the MCU 22, which determines at operation 212 if a reply has been received. At operation 414, the MCU 22 determines if the timer stopped, and if so halts use at operation 418. If the timer has not stopped, then at operation 416, the MCU 22 determines if the tip descriptor or optionally an expiration indicator was received, which in the case of the latter causes the MCU to halt use. At operation 420 the MCU 22 can optionally retrieve treatment parameters from memory based on information received in the tip descriptor, otherwise, all treatment parameters are received in the tip descriptor and probe is ready for use.

While the exemplary embodiments have been described in some detail for clarity of understanding and by way of example, a number of modifications, changes, and adaptations may be implemented and/or will be obvious to those as skilled in the art. Hence, the scope of the present invention is limited solely by the claims as follows.

What is claimed is:

1. A method for cryogenically treating tissue, the method comprising:
    detecting connection of a probe having a disposable secure processor (DSP) to a handpiece having a microcontroller unit (MCU) and a handpiece secure processor (HSP), the probe having at least one cryogenic treatment applicator, the probe being fluidly coupled to a closed coolant supply system within the handpiece via the connection;
    initiating an authentication process between the DSP and HSP using the MCU; and
    as a result of the authentication process, determining one of at least two predetermined results, the at least two predetermined results comprising that the probe is authorized or non-authorized.

2. The method of claim 1, wherein the authentication process by the HSP comprises:
    requesting a certificate from the DSP;
    validating the certificate;
    creating a nonce;
    encrypting the nonce with the public key in the certificate;
    sending a request to the DSP to decrypt the nonce using a private key;
    receiving the decrypted nonce from the DSP; and
    verifying the decrypted nonce.

3. The method of claim 2, wherein the probe is authorized after the HSP determines that the certificate is valid and the DSP has successfully decrypted the nonce or non-authorized after the DSP fails to provide a valid certificate to the HSP or to return a correctly decrypted nonce.

4. The method of claim 1, wherein the MCU and HSP are integrated as a single secure processor.

5. The method of claim 1, further comprising:
    requesting the DSP to determine expiration information; and
    based on the expiration information, determining one of:
        that the probe is expired or non-expired.

6. The method of claim 5, wherein, as a result that the probe is determined to be non-expired, retrieving data from the DSP containing procedural parameters or identification information for the MCU for operating the probe.

7. The method of claim 6, wherein the data comprises a tip descriptor that includes cooling cycle time parameters.

8. The method of claim 5, wherein determining one of that the probe is expired or non-expired comprises sending a request to the DSP to check the allowed remaining uses of the probe.

9. The method of claim 6, further comprising verifying a compatible tip connection prior to initiating a treatment protocol.

10. The method of claim 8, wherein after receiving the request the DSP determines the remaining allowable uses of the probe and provides the MCU with one of: an indication that the probe has no remaining uses available or an indication that the probe can be used.

11. The method of claim 10, wherein the DSP provides the MCU with the indication that the probe can be used.

12. The method of claim 11, further comprising updating a counter of the probe.

13. The method of claim 1, wherein as a result of the authentication process the probe is determined to be non-authorized for use.

14. The method of claim 13, further comprising transmitting a user alert using the MCU indicating that the probe is not authorized for use with the handpiece.

15. The method of claim 1, wherein each secure processor includes a certificate and the authentication process comprises performing an asymmetric key algorithm using the certificates.

16. The method of claim 1, wherein communication between the secure processors is encrypted during the authentication process.

17. The method of claim 1, wherein the probe is authorized and as a result the MCU opens the fluid connection between the probe and cryogen coolant supply system.

18. The method of claim 1, wherein the probe is authorized and as a result the MCU provides the probe with power to operate a heater of the probe.

19. A method for cryogenically treating tissue, the method comprising:
    detecting connection of a first type of probe having a first processor to a handpiece having a microcontroller unit (MCU), the handpiece being compatible with a plurality of different types of probes, the first type of probe having at least one cryogenic treatment applicator, the first type of probe being fluidly coupled to a closed coolant supply system within the handpiece via the connection;
    initiating a communication process between the first processor and the MCU, wherein the first processor provides a first type of tip descriptor to the MCU; and
    as a result of the communication process, initiating a first type of treatment protocol based on the first type of tip descriptor.

20. The method of claim 19, wherein the first type of treatment protocol is provided by the tip descriptor.

21. The method of claim 19, wherein the treatment protocol is retrieved from memory of the handpiece by the MCU based on identification of the tip descriptor.

22. The method of claim 19, wherein the plurality of different types of probes share the same type of cryogenic treatment applicator configuration.

23. The method of claim 19, wherein the tip descriptor comprises operating instructions to control metering of coolant to the cryogenic treatment applicator by way of a controllable valve.

24. The method of claim 23, wherein the operating instructions comprise the treatment protocol for timing opening and closing of the controllable valve.

25. The method of claim 19, wherein the tip descriptor includes test parameters.

26. The method of claim 19, wherein the tip descriptor includes expiration information.

27. The method of claim 26, wherein the tip descriptor includes an indication that the probe has no remaining uses available or an indication that the probe can be used.

28. The method of claim 19, further comprising initiating an authentication process between the first processor and a handpiece secure processor using the MCU to determine if the probe is authorized or non-authorized.

29. The method of claim 19, wherein the probe includes a heater and wherein the tip descriptor includes heater control parameters.

30. The method of claim 29, wherein the tip descriptor includes a target heater temperature.

31. The method of claim 19, wherein the at least one cryogenic treatment applicator comprises a sharpened or blunted needle.

32. A method for cryogenically treating tissue, the method comprising:
- detecting a first connection of a first type of probe having a first processor to a handpiece having a master control unit (MCU), the handpiece being compatible with a plurality of different types of probes, the first type of probe having at least one cryogenic treatment applicator, the first type of probe being fluidly coupled to a closed coolant supply system within the handpiece via the first connection;
- initiating a communication process between the first processor and the MCU, wherein the first processor provides a tip descriptor to the MCU, the first type of tip descriptor being specific to the first type of probe; and
- as a result of the communication process, initiating a first type of treatment protocol based on the tip descriptor;
- detecting a second connection of a second type of probe having a second processor to the handpiece after the first type of probe is decoupled from the handpiece, the second type of probe sharing the same type of cryogenic treatment applicator configuration as the first type of probe, the second type of probe being fluidly coupled to the closed coolant supply system within the handpiece via the second connection;
- initiating a communication process between the second processor and the MCU, wherein the second processor provides a second type of tip descriptor to the MCU; and
- as a result of the communication process, initiating a second type of treatment protocol based on the second type of tip descriptor, the second type of treatment protocol being different from the first type of treatment protocol.

\* \* \* \* \*